United States Patent [19]

Lunkenheimer et al.

[11] Patent Number: 4,968,714

[45] Date of Patent: Nov. 6, 1990

[54] FUNGICIDAL SUBSTITUTED 3-AMINO-2-PYRAZOLIN-5-ONES, COMPOSITIONS AND USE

[75] Inventors: Winfried Lunkenheimer, Wuppertal; Gerd Hänssler, Leverkusen, both of Fed. Rep. of Germany

[73] Assignee: Bayer Aktiengesellschaft, Leverkusen, Fed. Rep. of Germany

[21] Appl. No.: 481,487

[22] Filed: Feb. 16, 1990

[30] Foreign Application Priority Data

Feb. 21, 1989 [DE] Fed. Rep. of Germany ....... 3905312

[51] Int. Cl.$^5$ .................. A01N 43/56; A01N 43/40; C07D 231/52; C07D 401/12
[52] U.S. Cl. .................. 514/404; 514/227.8; 514/232.2; 514/236.5; 514/252; 514/256; 514/269; 514/318; 514/326; 514/341; 544/58.5; 544/58.6; 544/58.7; 544/82; 544/120; 544/121; 544/130; 544/131; 544/140; 544/238; 544/295; 544/296; 544/333; 544/357; 544/360; 544/364; 544/371; 546/193; 546/194; 546/211; 546/256; 546/279; 548/360
[58] Field of Search .................. 544/58.5, 58.6, 58.7, 544/82, 120, 296, 121, 333, 130, 357, 131, 360, 140, 364, 238, 295, 371; 546/193, 194, 211, 256, 279; 548/360; 514/227.8, 232.2, 236.5, 252, 256, 269, 318, 326, 341, 404

[56] References Cited

FOREIGN PATENT DOCUMENTS 0166171 1/1986 European Pat. Off. .

Primary Examiner—Robert W. Ramsuer
Attorney, Agent, or Firm—Sprung Horn Kramer & Woods

[57] ABSTRACT

Fungicidal substituted 3-amino-2-pyrazolin-5-ones of the formula

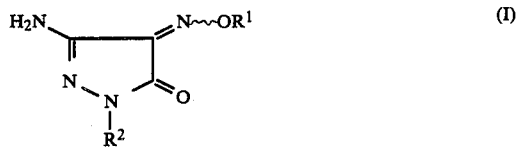

in which $R^1$ represents unsubstituted or substituted alkyl, unsubstituted or substituted alkenyl or alkinyl, or unsubstituted or substituted cycloalkyl or cycloalkenyl, $R^2$ represents hydrogen, unsubstituted or substituted alkyl, unsubstituted or substituted alkenyl or alkinyl, unsubstituted or substituted cycloalky or cycloalkenyl, unsubstituted or substituted aryl or unsubstituted or substituted heterocyclyl, or represents one of the radicals —CX—YR$^3$, —CXNR$^4$R$^5$,

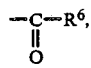

—SO$_2$NR$^4$R$^5$ or —SO$_2$R$^7$, $R^3$ represents unsubstituted or substituted alkyl or unsubstituted or substituted alkenyl or alkinyl, $R^4$ and $R^5$ are identical or different and represent hydrogen, unsubstituted or substituted alkyl, unsubstituted or substituted alkenyl or alkinyl or unsubstituted or substituted aryl or heterocyclyl, or together with the nitrogen atom to which they are bonded represent an unsubstituted or substituted heterocyclic ring which can contain further hetero atoms, $R^6$ represents hydrogen, unsubstituted or substituted alkyl, unsubstituted or substituted alkenyl or alkinyl, unsubstituted or substituted cycloalkyl or cycloalkenyl, unsubstituted or substituted aryl or unsubstituted or substituted heterocyclyl alkoxycarbonyl or phenylcarbonyl, $R^7$ represents unsubstituted or substituted alkyl or unsubstituted or substituted aryl and X and Y are identical or different and represent oxygen or sulphur.

13 Claims, No Drawings

FUNGICIDAL SUBSTITUTED 3-AMINO-2-PYRAZOLIN-5-ONES, COMPOSITIONS AND USE

The present invention relates to new substituted 3-amino-2-pyrazolin-5-one derivatives, to several processes for their preparation and to their use in pesticides, especially as fungicides.

It is already known that certain substituted 2-pyrazolin-5-one derivatives, such as, for example, 1,3-dimethyl-4-(2-chloromethyl-benzyloximino)-2-pyrazolin-5-one and 1,3-dimethyl-4-(4-phenyl-benzyloximino)-2-pyrazolin-5-one, have a good fungicidal action (cf. EP-OS (European Published Specification) No. 0,166,171). However, the action of these compounds is not always entirely satisfactory, in particular when low application rates and application concentrations are used.

New substituted 3-amino-2-pyrazolin-5-one derivatives of the general formula (I)

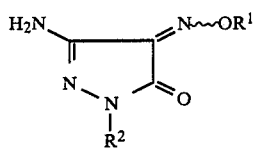

in which
$R^1$ represents unsubstituted or substituted alkyl, unsubstituted or substituted alkenyl or alkinyl, or unsubstituted or substituted cycloalkyl or cycloalkenyl,
$R^2$ represents hydrogen, unsubstituted or substituted alkyl, unsubstituted or substituted alkenyl or alkinyl, unsubstituted or substituted cycloalkyl or cycloalkenyl, unsubstituted or substituted aryl or unsubstituted or substituted heterocyclyl, or represents one of the radicals
—CX—YR$^3$, —CXNR$^4$R$^5$,

—SO$_2$NR$^4$R$^5$ or —SO$_2$R$^7$,
$R^3$ represents unsubstituted or substituted alkyl or unsubstituted or substituted alkenyl or alkinyl,
$R^4$ and $R^5$ are identical or different and represent hydrogen, unsubstituted or substituted alkyl, unsubstituted or substituted alkenyl or alkinyl or unsubstituted or substituted aryl or heterocyclyl, or together with the nitrogen atom to which they are bonded represent an unsubstituted or substituted heterocyclic ring which can contain further hetero atoms,
$R^6$ represents hydrogen, unsubstituted or substituted alkyl, unsubstituted or substituted alkenyl or alkinyl, unsubstituted or substituted cycloalkyl or cycloalkenyl, unsubstituted or substituted aryl or unsubstituted or substituted heterocyclyl, alkoxycarbonyl or phenylcarbonyl,
$R^7$ represents unsubstituted or substituted alkyl or unsubstituted or substituted aryl and
X and Y are identical or different and represent oxygen or sulphur
have been found.

The compounds of the formula (I) can be present as geometric isomers or isomer mixtures of various compositions.

The invention extends to the pure isomers as well as the isomer mixtures.

Furthermore, it has been found that the new substituted 3-amino-2-pyrazolin-5-one derivatives of the general formula (I)

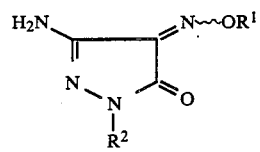

in which
$R^1$ represents unsubstituted or substituted alkyl, unsubstituted or substituted alkenyl or alkinyl, or unsubstituted or substituted cycloalkyl or cycloalkenyl,
$R^2$ represents hydrogen, unsubstituted or substituted alkyl, unsubstituted or substituted alkenyl or alkinyl, unsubstituted or substituted cycloalkyl or cycloalkenyl, unsubstituted or substituted aryl or unsubstituted or substituted heterocyclyl, or represents one of the radicals
—CX—YR$^3$, —CXNR$^4$R$^5$,

—SO$_2$NR$^4$R$^5$ or —SO$_2$R$^7$,
$R^3$ represents unsubstituted or substituted alkyl or unsubstituted or substituted alkenyl or alkinyl,
$R^4$ and $R^5$ are identical or different and represent hydrogen, unsubstituted or substituted alkyl, unsubstituted or substituted alkenyl or alkinyl or unsubstituted or substituted aryl or heterocyclyl, or together with the nitrogen atom to which they are bonded represent an unsubstituted or substituted heterocyclic ring which can contain further hetero atoms,
$R^6$ represents hydrogen, unsubstituted or substituted alkyl, unsubstituted or substituted alkenyl or alkinyl, unsubstituted or substituted cycloalkyl or cycloalkenyl, unsubstituted or substituted aryl or unsubstituted or substituted heterocyclyl, alkoxycarbonyl or phenylcarbonyl,
$R^7$ represents unsubstituted or substituted alkyl or unsubstituted or substituted aryl and
X and Y are identical or different and represent oxygen or sulphur,
are obtained when
(a) 2-cyano-2-oximino-acetic acid derivatives of the formula (II)

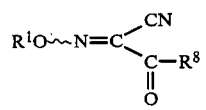

in which
$R^1$ has the abovementioned meaning and
$R^8$ represents lower alkoxy, preferably methoxy or ethoxy, or halogen, preferably chlorine,
are reacted with hydrazines of the formula (III)

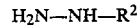

in which $R^2$ has the abovementioned meaning, if appropriate in the presence of a diluent, if appropriate in the presence of a base and if appropriate in the presence of a catalyst, or when (b) the 4-oximino-2-pyrazolin-5-one derivatives obtainable by process (a) of the general formula (Ia)

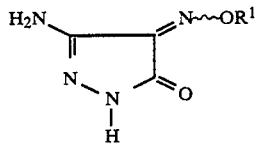

(Ia)

in which
  $R^1$ has the abovementioned meaning,
are reacted
(b1) with agents of the formula (IV)

$$R^{2-1}\text{-A} \qquad (IV)$$

in which
  $R^{2-1}$ represents unsubstituted or substituted alkyl, unsubstituted or substituted alkenyl or alkinyl, unsubstituted or substituted cycloalkyl, unsubstituted or substituted cycloalkenyl or unsubstituted or substituted heterocyclyl and
  A represents an electron-withdrawing leaving group,
or
(b2) with acylating agents of the formula (Va)

$$R^{2-2}\text{-Z} \qquad (Va)$$

in which
  $R^{2-2}$ represents one of the radicals
  $-CX-YR^3$, $-CXNR^4R^5$,

,
  $-SO_2NR^4R^5$ or $-SO_2R^7$,
  Z represents a customary leaving group, such as halogen, $-O-CO-R^{2-2}$, $-O-CO-R^{2-1}$, $-OR^{2-1}$, $-SR^{2-1}$, carboxymethoxy or carboxymethylthio and
  $R^3$, $R^4$, $R^5$, $R^6$, $R^7$, X and Y have the abovementioned meanings,
or
(b3) with acylating agents of the formula (Vb)

$$R^{2-3}-N=C=X \qquad (Vb)$$

in which
  $R^{2-3}$ represents unsubstituted or substituted alkyl, unsubstituted or substituted alkenyl or alkinyl, unsubstituted or substituted cycloalkyl or cycloalkenyl, unsubstituted or substituted aryl or substituted or unsubstituted heterocyclyl and
  X represents oxygen or sulphur,
if appropriate in the presence of a diluent, if appropriate in the presence of a base and if appropriate in the presence of a catalyst; or when
(c) 4-oximino-2-pyrazolin-5-one derivatives of the formula (VI)

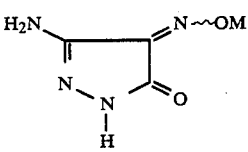

(VI)

in which
  M represents hydrogen or an alkali metal cation, are reacted with alkylating agents of the formula (VII)

$$R^1\text{-A} \qquad (VII)$$

in which
  $R^1$ has the abovementioned meaning and
  A represents an electron-withdrawing leaving group, if appropriate in the presence of a diluent and if appropriate in the presence of a catalyst.

Finally, it has been found that the new substituted 3-amino-2-pyrazolin-5-one derivatives of the formula (I) exhibit a powerful biological action. In this context, the compounds of the formula (I) according to the invention, surprisingly, show a better fungicidal action, for example, than the substituted 2-pyrazolin-5-one derivatives which are known from the prior art and which are compounds of similar structure and a similar type of action. The substances according to the invention thus represent an enrichment of the art.

Unsubstituted or substituted alkyl in the definition of $R^1$ and $R^2$, and alkyl in the definition of $R^3$, $R^4$, $R^5$, $R^6$ and $R^7$ in the general formulae represent straight-chain or branched alkyl preferably having 1 to 10, particularly preferably 1 to 8 and very particularly preferably 1 to 6 carbon atoms. Examples which may be mentioned are unsubstituted or substituted methyl, ethyl, n-propyl, i-propyl, n-butyl, sec-butyl, i-butyl, tert-butyl, n-pentyl, i-pentyl and t-pentyl.

Unsubstituted or substituted alkenyl in the definitions of $R^1$ and $R^2$, and alkenyl in the definition of $R^3$, $R^4$, $R^5$ and $R^6$ in the general formulae represent straight-chain or branched alkenyl, preferably having 2 to 8, particularly preferably 2 to 6, and in particular 2 to 4, and very particularly preferably 3, carbon atoms. Examples which may be mentioned are unsubstituted or substituted vinyl, allyl, 2-butenyl, 3-butenyl and 1-methallyl.

The term unsubstituted or substituted alkinyl in the definitions of $R^1$ and $R^2$ and alkinyl in the definition of $R^3$, $R^4$, $R^5$ and $R^6$ in the general formulae is taken to mean straight-chain or branched alkinyl, preferably having 2 to 6, in particular 2 to 4, and particularly preferably 3, carbon atoms. Examples which may be mentioned are unsubstituted or substituted ethinyl, 2-propinyl, 2-butinyl, 3-butinyl and 1-methyl-2-propinyl.

Unsubstituted or substituted cycloalkyl in the definitions $R^1$ and $R^2$ and cycloalkyl in the definition of $R^6$ represent cycloalkyl, preferably having 3 to 8, in particular 3, 5 or 6, carbon atoms. Examples which may be mentioned are unsubstituted or substituted cyclopropyl, cyclobutyl, cyclopentyl, cyclohexyl and cycloheptyl.

Unsubstituted or substituted cycloalkenyl in the definitions of $R^1$ and $R^2$ and cycloalkenyl in the definitions of $R^4$, $R^5$ and $R^6$ represent cycloalkenyl, preferably having 5 or 6, in particular 6, carbon atoms. Examples which may be mentioned are unsubstituted or substituted cyclopentenyl and cyclohexenyl.

The term unsubstituted or substituted aryl in the definition of $R^2$ in the general formulae and aryl in the definition of $R^4$, $R^5$, $R^6$ and $R^7$ is taken to mean aryl, preferably having 6 to 10 carbon atoms in the aryl moiety. Examples which may be mentioned are optionally substituted phenyl or naphthyl, in particular phenyl.

Unsubstituted or substituted heterocyclyl in the definition of $R^2$ and heterocyclyl or heterocyclic ring in the definitions of $R^4$, $R^5$ and $R^6$ represent a 5- or 6-membered ring which contains one or more hetero atoms, preferably 1 to 3 identical or different hetero atoms, and the corresponding benzo-fused rings. Hetero atoms which may preferably be mentioned are oxygen, sulphur and nitrogen; examples which may be mentioned are: furanyl, thienyl, tetrahydrofuranyl, thiolanyl, pyridyl, indolyl, N-methylpyrrolyl, pyrimidyl, sulpholanyl, morpholinyl, thiazolyl, benzothiazolyl, thiadiazolyl, isoxazolyl, pyrazinyl, oxazolinyl, pyrrolidinyl, imidazolinyl, piperidinyl, thiomorpholinyl, 1,3-oxazanyl, 1,3-diazanyl.

Unsubstituted or substituted alkoxycarbonyl in the definition of $R^6$ represents straight-chain or branched alkoxycarbonyl having 1 to 4, preferably 1 or 2, carbon atoms in the alkoxy radical; examples which may be mentioned are: methoxycarbonyl, ethoxycarbonyl, n-propoxycarbonyl, i-propoxycarbonyl and n-, i-, sec- and t-butoxycarbonyl.

The substituted radicals of the general formulae can carry one or more, preferably 1 to 3, in particular 1 or 2, identical or different substituents. The following substituents may be listed by way of example and as preferred: alkyl itself or as a constituent of alkylcarbonyl, preferably having 1 to 4, in particular 1 or 2, carbon atoms, such as methyl, ethyl, n- or i-propyl and n-, i- and t-butyl; alkoxy, preferably having 1 to 4, in particular 1 or 2, carbon atoms, such as methoxy, ethoxy, n- and i-propyloxy and n-, i-, sec- and t-butyloxy;

In general, halogen as a substituent preferably denotes fluorine, chlorine, bromine and iodine, in particular fluorine, chlorine and bromine, and particularly preferably fluorine and chlorine.

Unsubstituted or substituted cycloalkyl as a substituent represents cycloalkyl, preferably having 3 to 8, in particular 3, 5 or 6 carbon atoms.

Examples which may be mentioned are optionally substituted cyclopropyl, cyclobutyl, cyclopentyl, cyclohexyl and cycloheptyl.

Unsubstituted or substituted cycloalkenyl as a substituent represents cycloalkenyl, preferably having 5 or 6, in particular 6, carbon atoms.

Examples which may be mentioned are unsubstituted or substituted cyclopentenyl and cyclohexenyl.

In general, unsubstituted or substituted heterocyclyl as a substituent represents a 5- or 6-membered ring which contains one or more hetero atoms, preferably 1 to 3 identical or different hetero atoms. Hetero atoms which may preferably be mentioned are oxygen, sulphur and nitrogen; examples which may be mentioned are: furanyl, thienyl, tetrahydrofuranyl, thiolanyl, pyrazolyl, 1,2,4-triazolyl, oxiranyl, 1,3-dioxolanyl, phthalimidyl, 2-pyrrolidony, 3-methyl-2-oxazolidinonyl,N-methylpideridinyl, tetrahydropyrrolyl, morpholinyl, 1,3-dioxanyl, 4-methyl-thiazolyl,4-methyl-oxazolyl,4,5-dihydrooxazolyl, 4,5-dihydrothiazolyl, pyrimidinyl, 1,2,4-thiadiazolyl, 1,3,4-thiadiazolyl and 1,3,4-oxadiazolyl.

Specifically, the substituents for aryl radicals as such, or in compositions such as aryloxy or aralkoxy and for the heterocyclic rinqs have the meanings indicated below.

In general, halogen as a substituent of the radicals represents fluorine, chlorine, bromine and iodine, preferably represents fluorine, chlorine and bromine, and particularly preferably represents fluorine and chlorine.

In general, alkyl as a substituent of the radicals represents straight-chain or branched alkyl, preferably having 1 to 6, particularly preferably having 1 to 4, carbon atoms, with methyl, ethyl and t-butyl being very particularly preferred. The enumeration given by way of example corresponds to that indicated further above.

In general, alkoxy as a substituent of the radicals represents straight-chain or branched alkoxy having 1 to 6, preferably having 1 to 3, carbon atoms; examples which may be mentioned are: methoxy, ethoxy, n- and i-propoxy, n-, i-, sec- and t-butoxy, n-hexoxy and i-hexoxy.

In general, halogenoalkyl and halogenoalkoxy as substituents in the radicals represent straight-chain or branched radicals, each having 1 to 4 carbon atoms, particularly preferably having 1 or 2 carbon atoms, and in each case 1 to 5 identical or different halogen atoms as defined under halogen; examples which may be mentioned are: fluoromethyl, chloromethyl, bromomethyl, fluoroethyl, chloroethyl, bromoethyl, fluoro-n-propyl, chloro-n-propyl, difluoromethyl, trifluoromethyl, dichloromethyl, trichloromethyl, difluoroethyl, trifluoroethyl, trichloroethyl,chloro-difluoro-methyl, trifluorochloroethyl, chlorobutyl, fluorobutyl, fluoromethoxy, chloromethoxy, bromomethoxy, fluoroethoxy, chloroethoxy, bromoethoxy, fluoropropoxy, chloropropoxy, bromopropoxy, fluorobutoxy, chlorobutoxy, fluoro-i-propoxy, chloro-i-propoxy, difluoromethoxy, trifluoromethoxy, dichloromethoxy, trichloromethoxy, difluoroethoxy, trifluoroethoxy, tetrafluoroethoxy, trichloroethoxy, chlorodifluoromethoxy and trifluorochloroethoxy.

Mono- or di-alkylamino represents an amino group having 1 or 2 alkyl groups, preferably 2 alkyl groups, which in each case can be straight-chain or branched and preferably contain 1 to 5, in particular 1 to 3, carbon atoms, with methyl, ethyl, n- and i-propyl being mentioned. Dimethylamino, diethylamino, di-n-propylamino and di-i-propylamino may be mentioned by way of example.

Formula (I) provides a general definition of the 3-amino-2-pyrazolin-5-one derivatives according to the invention. Preferably, in this formula (I)

$R^1$ represents straight-chain or branched alkyl which has 1 to 10 carbon atoms and which is unsubstituted or monosubstituted to pentasubstituted by identical or different substituents, suitable substituents being the following: fluorine, chlorine, bromine, iodine, cyano, —COOH, —COOR$^3$, —CONR$^4$R$^5$, —OR$^6$, —SR$^6$, alkylcarbonyl having 1 to 9 carbon atoms, phenylcarbonyl which is unsubstituted or monosubstituted to trisubstituted by identical or different halogen substituents, phenyl which is unsubstituted or monosubstituted to pentasubstituted by identical or different substituents, phenyl substituents which may be mentioned being: halogen, nitro, alkyl and alkoxy, each having 1 to 4 carbon atoms, halogenoalkyl and halogenoalkoxy, each having 1 or 2 carbon atoms and 1 to 5 identical or different halogen atoms; amino, alkylamino and dialkylamino, each having 1 to 4 carbon atoms in the individual alkyl moieties, aryloxy and aralkoxy, each having 6 to 12 carbon atoms in the aryl moiety and 1 to 4 carbon atoms in the alkoxy moiety; further alkyl substituents are cycloalkyl or cycloalkenyl which have 3 to 6 carbon atoms and which are unsubstituted or monosubstituted to pentasubstituted by identical or different substituents from the series comprising chlorine and alkyl having 1 to 4 carbon atoms, or 3- to 6-membered heterocyclyl which has 1 to 3 identical or different hetero atoms, such as nitrogen, oxygen and sulphur atoms, and which is unsubstituted or monosubstituted to pentasubstituted by identical or different substituents from the series comprising halogen, hydroxyl, oxo, alkyl and alkoxy having 1 to 4 carbon atoms; $R^1$ furthermore preferably represents straight-chain or branched alkenyl or alkinyl, each of which has 2 to 6 carbon atoms and each of which is unsubstituted or monosubstituted to trisubstituted by identical or different substituents, suitable substituents which may be mentioned being: phenyl which is unsubstituted or monosubstituted to pentasubstituted by identical or different substituents from the series comprising halogen, alkyl and alkoxy having 1 to 4 carbon atoms; $R^1$ furthermore preferably represents cycloalkyl which has 3 to 6 carbon atoms or cycloalkenyl which has 5 to 7 carbon atoms, each of these radicals being unsubstituted or monosubstituted to pentasubstituted by identical or different substituents from the series comprising chlorine, alkyl or alkoxy having 1 to 4 carbon atoms;

$R^2$ represents hydrogen, or represents straight-chain or branched alkyl which has 1 to 6 carbon atoms and which is unsubstituted or monosubstituted to pentasubstituted by identical or different substituents, suitable substituents being the following: fluorine, chlorine, bromine, iodine, cyano, —COOH, —COOR$^3$, —CONR$^4$R$^5$, —OR$^6$, —SR$^6$, alkylcarbonyl having 1 to 9 carbon atoms, phenylcarbonyl which is unsubstituted or monosubstituted to trisubstituted by identical or different halogen substituents, or phenyl which is unsubstituted or monosubstituted to pentasubstituted by identical or different substituents, phenyl substituents which may be mentioned being: halogen, nitro, or alkyl and alkoxy, each having 1 to 4 carbon atoms, or halogenoalkyl and halogenoalkoxy, each having 1 or 2 carbon atoms and 1 to 5 identical or different halogen atoms, or amino, or alkylamino and dialkylamino, each having 1 to 4 carbon atoms in the individual alkyl moieties, or aryloxy and aralkoxy, each having 6 to 12 carbon atoms in the aryl moiety and 1 to 4 carbon atoms in the alkoxy moiety; further alkyl substituents are cycloalkyl which has 3 to 6 carbon atoms and which is unsubstituted or monosubstituted to pentasubstituted by identical or different substituents from the series comprising chlorine and alkyl having 1 to 4 carbon atoms, or 3- to 6-membered heterocyclyl which has 1 to 3 identical or different hetero atoms, such as nitrogen, oxygen and sulphur atoms, and which is unsubstituted or monosubstituted to pentasubstituted by identical or different substituents from the series comprising halogen, hydroxyl, oxo, alkyl and alkoxy having 1 to 4 carbon atoms; $R^2$ furthermore preferably represents straight-chain or branched alkenyl or alkinyl, each of which has 2 to 6 carbon atoms and each of which is unsubstituted or monosubstituted to trisubstituted by identical or different substituents, suitable substituents which may be mentioned being: phenyl which is unsubstituted or monosubstituted to pentasubstituted by identical or different substituents from the series comprising halogen and alkyl having 1 to 4 carbon atoms; $R^2$ furthermore preferably represents cycloalkyl which has 3 to 6 carbon atoms or cycloalkenyl which has 5 to 7 carbon atoms, each of these radicals being unsubstituted or monosubstituted to pentasubstituted by identical or different alkyl substituents having 1 to 4 carbon atoms: $R^2$ furthermore represents aryl which has 6 to 12 carbon atoms and which is unsubstituted or monosubstituted to pentasubstituted by identical or different substituents, suitable substituents which may be mentioned being: halogen, nitro, or alkyl or alkoxy, each having 1 to 4 carbon atoms, or halogenoalkyl or halogenoalkoxy, each having 1 or 2 carbon atoms in the alkyl moiety and 1 to 5 identical or different halogen atoms;

$R^2$ furthermore preferably represents 3- to 6-membered heterocyclyl which has 1 to 3 identical or different hetero atoms, such as nitrogen, oxygen and sulphur atoms, and which is unsubstituted or monosubstituted to pentasubstituted by identical or different substituents from the series comprising halogen, hydroxyl, oxo and alkyl and alkoxy, each having 1 to 4 carbon atoms, or represents one of the radicals —CX—YR$^3$, —CXNR$^4$R$^5$, —CO—R$^6$, —SO$_2$—NR$^4$R$^5$ or —SO$_2$R$^7$, where X and Y are identical or different and represent oxygen or sulphur, $R^3$ represents straight-chain or branched alkyl which has 1 to 6 carbon atoms and which is unsubstituted or monosubstituted to pentasubstituted by identical or different substituents, suitable substituents which may be mentioned being: halogen, phenyl which is unsubstituted or monosubstituted to pentasubstituted by identical or different substituents, suitable phenyl substituents being halogen, nitro, or alkyl and alkoxy, each having 1 to 4 carbon atoms, or halogenoalkyl or halogenoalkoxy, each having 1 or 2 carbon atoms and 1 to 5 identical or different halogen atoms, or amino, or alkylamino and dialkylamino, each having 1 to 4 carbons in the individual alkyl moieties, or aryloxy and aralkoxy, each having 6 to 12 carbon atoms in the aryl moiety and 1 to 4 carbon atoms in the alkoxy moiety, and furthermore represents cycloalkyl or cycloalkenyl, in each case having 3 to 6 carbon atoms; $R^3$ furthermore represents straight-chain or branched alkenyl or alkinyl, each having 3 to 6 carbon atoms, $R^4$ and $R^5$ in each case are identical or different and represent hydrogen or represent alkyl which has 1 to 6 carbon atoms and which is unsubstituted or monosubstituted or disubstituted by identical or different substituents, suitable substituents being the following: alkoxy having 1 to 4 carbon atoms, phenyl which is unsubstituted or monosubstituted to pentasubstituted by identical or different substituents from the series comprising halogen, nitro and alkyl and alkoxy, each having 1 to 4 carbon atoms, or halogenoalkyl and halogenoalkoxy, each having 1 or 2 carbon atoms and 1 to 5 identical or different halogen atoms, or amino, or alkylamino and dialkylamino, each having 1 to 4 carbon atoms in the individual alkyl moieties, or aryloxy and aralkoxy, each having 6 to 12 carbon atoms in the aryl moiety and 1 to 4 carbon atoms in the alkoxy moiety, or represent cycloalkyl or cycloalkenyl, each of which has 3 to 6 carbon atoms, $R^4$ and $R^5$ furthermore represent alkenyl or alkinyl, each of which has 3 to 6 carbon atoms, or represent phenyl which is unsubstituted or monosubstituted to pentasubstituted by identical or different substituents, suitable phenyl substituents being the substituents mentioned above in the case of $R^4$ and $R^5$ as phenyl substituents, or represent 3- to 6-membered heterocyclyl which has 1 to 3 identical or different hetero atoms, such as nitrogen, oxygen and sulphur, and which is monosubstituted to trisubstituted by identical or different substituents, suitable substituents being the following: halogen, hydroxyl, or alkyl or alkoxy, each having 1 to 4 carbon atoms, and oxo; furthermore, $R^4$ and $R^5$ together with the nitrogen atom to which they are bonded represent a 5- or 6-membered heterocyclic ring which can contain 1 or 2 further identical or different hetero atoms, such as nitrogen, oxygen or sulphur, and which is unsubstituted or monosubstituted to trisubstituted by identical or different substituents, suitable substituents being halogen, hydroxyl and alkyl and alkoxy, each having 1 to 4 carbon atoms, and oxo, $R^6$ represents hydrogen or represents straight-chain or branched alkyl which has 1 to 6 carbon atoms and which is unsubstituted or monosubstituted to pentasubstituted by identical or different substituents, suitable substituents being: halogen, alkoxy having 1 to 4 carbon atoms, cycloalkyl which has 3 to 6 carbon atoms and which is unsubstituted or substituted, phenyl which is unsubstituted or monosubstituted to trisubstituted, suitable substituents being those mentioned above in the case of $R^4$ and $R^5$ as phenyl substituents; $R^6$ furthermore represents alkenyl or alkinyl, each of which has 2 to 6 carbon atoms, cycloalkyl which has 3 to 6 carbon atoms, phenyl which is unsubstituted or monosubstituted to trisubstituted by identical or different substituents, suitable phenyl substituents being those substituents mentioned above in the case of $R^4$ and $R^5$ as phenyl substituents, or 3- to 6-membered heterocyclyl which has 1 to 3 identical or different hetero atoms, such as nitrogen, oxygen and sulphur, and which is unsubstituted or monosubstituted to trisubstituted by identical or different substituents, suitable substituents being halogen, hydroxyl or alkyl or alkoxy, each having 1 to 4 carbon atoms, or oxo, and furthermore represents alkoxycarbonyl which has 1 or 2 carbon atoms, or phenylcarbonyl, $R^7$ represents alkyl which has 1 to 6 carbon atoms and which is unsubstituted or monosubstituted to pentasubstituted by chlorine, or represents phenyl which is unsubstituted or monosubstituted to trisubstituted by identical or different substituents, suitable phenyl substituents being the substituents mentioned above in the cases of $R^4$ and $R^5$ as phenyl substituents.

Particularly preferred compounds of the formula (I) are those in which $R^1$ represents unsubstituted alkyl which has 1 to 8 carbon atoms, or represents straight-chain or branched alkyl which has 1 to 5 carbon atoms and which is monosubstituted to trisubstituted by identical or different substituents, suitable substituents being the following: fluorine, chlorine, bromine, iodine, cyano, —COOH, —COOR$^3$, —CONR$^4$R$^5$, —OR$^6$, —SR$^6$, alkylcarbonyl having 1 to 7 carbon atoms, phenylcarbonyl which is unsubstituted or monosubstituted or disubstituted by halogen, or phenyl which is unsubstituted or monosubstituted to trisubstituted by identical or different substituents from the series comprising fluorine, chlorine, nitro, methyl, methoxy, trifluoromethyl, trifluoromethoxy, amino, methylamino, dimethylamino, phenyloxy and phenylmethoxy, further alkyl substituents are cyclopropyl, cyclopentyl, cyclohexyl, cyclopentenyl or cyclohexenyl, each of which is unsubstituted or monosubstituted to trisubstituted by methyl or chlorine, and heterocyclic rings of the formulae

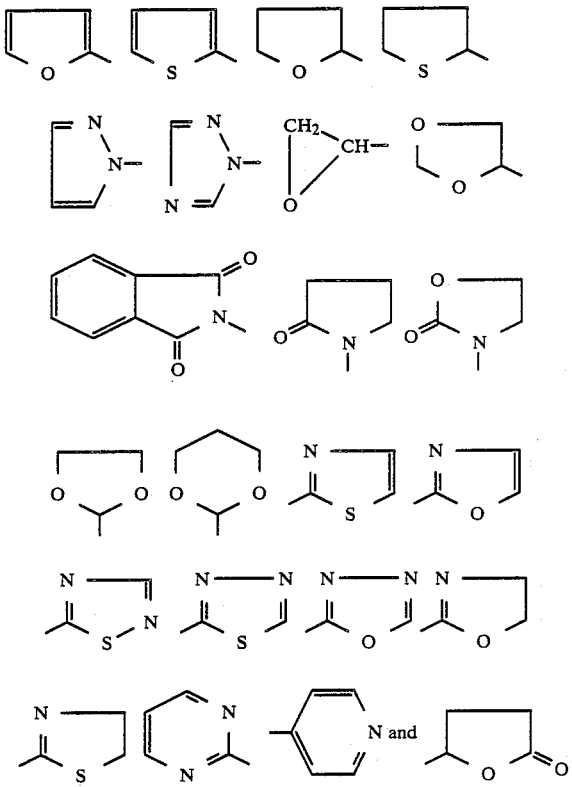

which are unsubstituted or monosubstituted to trisubstituted by identical or different substituents from the series comprising fluorine, chlorine, methyl, methoxy or hydroxyl, $R^1$ furthermore represents allyl or propargyl, each of which is monosubstituted or disubstituted, substituents which may be mentioned being phenyl which is unsubstituted or monosubstituted to trisubstituted by identical or different substituents from the series comprising fluorine, chlorine, methyl and methoxy. $R^1$ furthermore represents cyclopropyl, cyclopentyl, cyclohexyl, cyclopentenyl or cyclohexenyl, each of which is unsubstituted or monosubstituted to trisubstituted by chlorine, methyl or methoxy;

$R^2$ represents hydrogen, or represents straight-chain or branched alkyl which has 1 to 4 carbon atoms and which is unsubstituted or monosubstituted to trisubstituted by identical or different substituents, suitable substituents being the following: fluorine, chlorine, bromine, iodine, cyano, —COOH, —COOR$^3$, —CONR$^4$R$^5$, —OR$^6$, —SR$^6$, alkylcarbonyl having 1 to 7 carbon atoms, phenylcarbonyl which is unsubstituted or monosubstituted to trisubstituted by identical or different halogen substituents, or phenyl which is unsubstituted or monosubstituted to trisubstituted by identical or different substituents from the series comprising fluorine, chlorine, nitro, methyl, methoxy, trifluoromethyl, trifluoromethoxy, amino, methylamino, dimethylamino, phenyloxy and phenylalkoxy having 1 or 2 carbon atoms in the alkoxy moiety; further alkyl substituents are cyclopropyl, cyclopentyl, cyclohexyl, cyclopentenyl or cyclohexenyl, each of which is unsubstituted or monosubstituted to trisubstituted by methyl or chlorine, or heterocyclic rings of the formulae

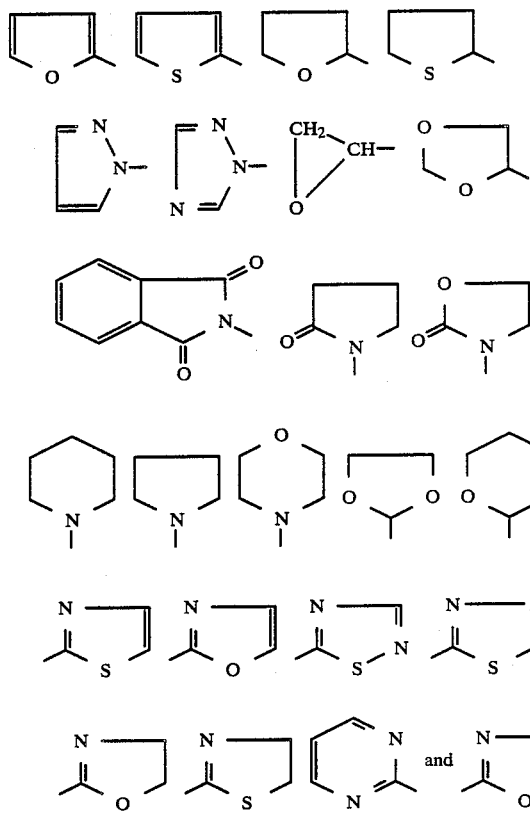

which are unsubstituted or monosubstituted to trisubstituted by identical or different substituents from the series comprising fluorine, chlorine, methyl, methoxy or hydroxyl, $R^2$ furthermore represents allyl or propargyl, each of which is monosubstituted or disubstituted by identical or different substituents, suitable substituents which may be mentioned being phenyl which is unsubstituted or monosubstituted to trisubstituted by identical or different substituents from the series comprising fluorine, chlorine, methyl or methoxy; $R^2$ furthermore represents cyclopropyl, cyclopentyl, cyclohexyl, cyclopentenyl or cyclohexenyl, each of which is unsubstituted or monosubstituted to trisubstituted by methyl or methoxy;

$R^2$ furthermore represents phenyl which is unsubstituted or monosubstituted to trisubstituted by identical or different substituents, suitable substituents which may be mentioned being: fluorine, chlorine, nitro, methyl, methoxy, trifluoromethyl or trifluoromethoxy, $R^2$ furthermore represents heterocyclic rings of the formulae

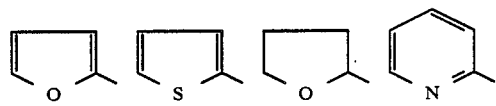

-continued

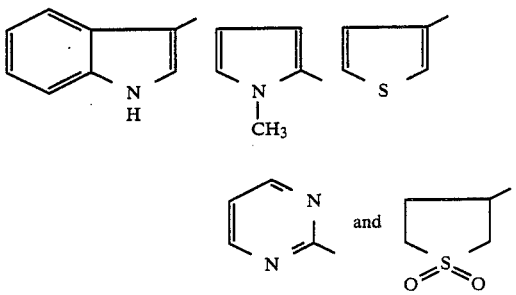

which are unsubstituted or monosubstituted to trisubstituted by identical or different substituents from the series comprising fluorine, chlorine, hydroxyl, oxo, methyl or methoxy, or represents one of the radicals $-CX-YR^3$, $-CXNR^4R^5$, $-COR^6$, $-SO_2-NR^4R^5$ or $-SO_2R^7$, where X and Y are identical or different and represent oxygen or sulphur, $R^3$ represents straight-chain or branched alkyl which has 1 to 4 carbon atoms and which is unsubstituted or monosubstituted to trisubstituted by identical or different substituents, suitable substituents being the following: fluorine, chlorine, bromine, iodine, phenyl which is unsubstituted or monosubstituted to trisubstituted by identical or different substituents from the series comprising fluorine, chlorine, nitro, methyl, methoxy, trifluoromethyl, trifluoromethoxy, amino, methylamino, dimethylamino, phenyloxy and phenylalkoxy having 1 or 2 carbon atoms in the alkyl moiety, and cyclopropyl, cyclopentyl, cyclohexyl, cyclopentenyl and cyclohexenyl, each of which is unsubstituted or monosubstituted to trisubstituted by methyl; $R^3$ furthermore represents allyl or propargyl, $R^4$ and $R^5$ are identical or different and represent hydrogen, or represent alkyl which has 1 to 4 carbon atoms and which is unsubstituted or monosubstituted or disubstituted by identical or different substituents, suitable substituents being the following: methoxy, ethoxy, phenyl which is unsubstituted or monosubstituted to trisubstituted by identical or different substituents from the series comprising fluorine, chlorine, bromine, iodine, nitro, methyl, methoxy, trifluoromethyl, trifluoromethoxy, amino, methylamino, dimethylamino, phenoxy and phenylmethoxy;

$R^4$ and $R^5$ furthermore represent allyl, propargyl, cyclopropyl, cyclopentyl, cyclohexyl, cyclopentenyl, cyclohexenyl and phenyl which is unsubstituted or monosubstituted to trisubstituted by identical or different substituents, suitable phenyl substituents being the substituents mentioned above in the cases of $R^4$ and $R^5$ as phenyl substituents, or furthermore represent heterocyclic rings of the formulae

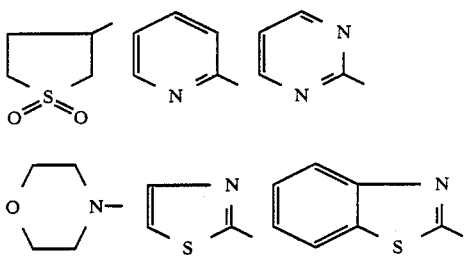

-continued

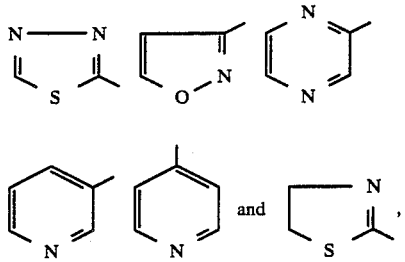

which are monosubstituted to trisubstituted by identical or different substituents from the series comprising fluorine, chlorine, methyl, methoxy, hydroxyl or oxo, or $R^4$ and $R^5$ furthermore together with the nitrogen atom to which they are bonded represent oxazoline, pyrolidine, imidazoline, piperazine, morpholine, thiomorpholine, 1,3-oxazane or 1,3-diazane, each of which is unsubstituted or substituted, suitable substituents being fluorine, chlorine, bromine, iodine, hydroxyl, methyl, methoxy and oxo, $R^6$ represents hydrogen, or represents straight-chain or branched alkyl which has 1 to 4 carbon atoms and which is unsubstituted or monosubstituted to trisubstituted by identical or different substituents, suitable substituents being: fluorine, chlorine, bromine, iodine, methoxy, cyclopropyl, cyclopentyl, cyclohexyl, phenyl which is unsubstituted or monosubstituted or disubstituted by identical or different substituents, suitable phenyl substituents being those mentioned above in the cases of $R^4$ and $R^5$ as phenyl substituents; furthermore represents allyl or propargyl, cyclopropyl, cyclopentyl or cyclohexyl, or represents phenyl which is unsubstituted or monosubstituted or disubstituted by identical or different substituents, suitable phenyl substituents being the substituents mentioned above in the cases of $R^4$ and $R^5$ as phenyl substituents; furthermore represents heterocyclic rings of the formulae

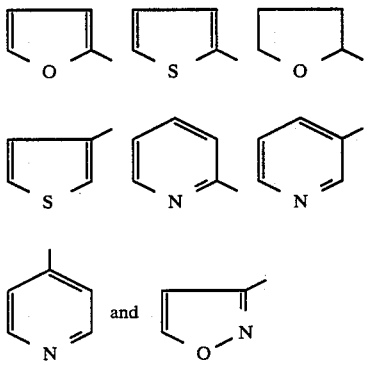

which are unsubstituted or monosubstituted to trisubstituted by identical or different substituents from the series comprising fluorine, chlorine, bromine, iodine, hydroxyl, oxo, methyl and methoxy, and furthermore represents methoxycarbonyl or ethoxycarbonyl or phenylcarbonyl, $R^7$ represents alkyl which has 1 to 4 carbon atoms and which is unsubstituted or monosubstituted to trisubstituted by chlorine, or represents phenyl which is unsubstituted or monosubstituted to trisubstituted by identical or different substituents, suitable phenyl substituents being the substituents mentioned above in the cases of $R^4$ and $R^5$ as phenyl substituents.

Very particularly preferred compounds of the formula (I) are those in which $R^1$ represents unsubstituted alkyl which has 1 to 8 carbon atoms, or represents methyl, ethyl or n- or i-propyl, each of which is monosubstituted or disubstituted by identical or different substituents, suitable substituents being the following: fluorine, cyano, —COOH, —COOR³, —CONR⁴R⁵, —OR⁶, —SR⁶, alkylcarbonyl which has 1 to 5 carbon atoms, phenylcarbonyl which is unsubstituted or monosubstituted or disubstituted by identical or different substituents from the series comprising fluorine, chlorine and bromine, or phenyl which is unsubstituted or monosubstituted to trisubstituted by identical or different substituents from the series comprising fluorine, chlorine, nitro, methyl, methoxy, trifluoromethyl, methylamino, dimethylamino and phenylmethoxy; further alkyl substituents are cyclopropyl, cyclohexyl or cyclohexenyl, each of which is unsubstituted or monosubstituted or disubstituted by methyl or chlorine, or heterocyclic rings of the formulae

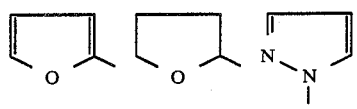

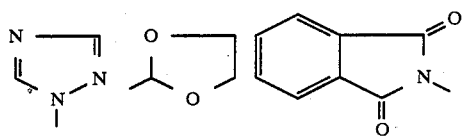

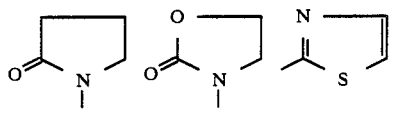

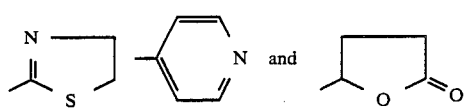

which are unsubstituted or monosubstituted to trisubstituted by methyl, $R^1$ furthermore represents allyl or propargyl, each of which is substituted by phenyl, or represents cyclohexyl, cyclopropyl or cyclohexenyl, each of which is unsubstituted or monosubstituted or disubstituted by methyl or chlorine, $R^2$ represents hydrogen, or represents methyl or ethyl, each of which is unsubstituted or monosubstituted to trisubstituted by identical or different substituents, suitable substituents being the following: fluorine, chlorine, cyano, —COOH, —COOR³, —CONR⁴R⁵, —OR⁶, —SR⁶, alkylcarbonyl which has 1 to 5 carbon atoms, phenyl, cyclopropyl, 1,3-dioxolan-2-yl, 1,2,4-triazol-1-yl or phenylcarbonyl which is unsubstituted or monosubstituted or disubstituted by identical or different substituents from the series comprising fluorine, chlorine or bromine; $R^2$ furthermore represents allyl or propargyl, or represents cyclohexyl or phenyl which is unsubstituted or monosubstituted or disubstituted by identical or different substituents from the series comprising chlorine, methyl or methoxy, or represents one of the radicals —CX—YR³, —CXNR⁴R⁵, —COR⁶, —SO₂—NR⁴R⁵, —SO₂R⁷ or

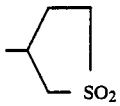

where
X and Y are identical or different and represent oxygen or sulphur,
R³ represents methyl, ethyl, n- or i-propyl or n-, i-, s- or t-butyl,
R⁴ represents hydrogen, methyl, ethyl, n- or i-propyl, n-, i-, s- or t-butyl or phenyl,
R⁵ represents hydrogen, methyl, ethyl, n- or i-propyl, n-, i-, s- or t-butyl or phenyl,
R⁶ represents hydrogen or methyl, ethyl, n- or i-propyl or n-, i-, s- or t-butyl, each of which is unsubstituted or monosubstituted to trisubstituted by fluorine, chlorine, methoxy or phenyl, R⁶ furthermore represents phenyl, methoxycarbonyl, ethoxycarbonyl or phenylcarbonyl and
R⁷ represents methyl, ethyl, n- or i-propyl or n-, i-, s- or t-butyl, or represents phenyl which is unsubstituted or monosubstituted or disubstituted by methyl.

Furthermore, very particularly preferred compounds of the formula (I) are those in which
R¹ represents straight-chain or branched alkyl which has 1 to 6 carbon atoms and which is unsubstituted, or represents methyl, ethyl or n- or i-propyl, each of which is monosubstituted or disubstituted by identical or different substituents, substituents which may be mentioned being: fluorine, cyano, —COOH, —COOR³, —CONR⁴R⁵, —OR⁶, —SR⁶, alkylcarbonyl which has 1 to 5 carbon atoms in the alkyl moiety, phenylcarbonyl which is unsubstituted or monosubstituted or disubstituted by identical or different bromine substituents, phenyl which is unsubstituted or monosubstituted to trisubstituted by identical or different substituents from the series comprising chlorine, methyl, methoxy, nitro, dimethylamino, benzyloxy and trifluoromethyl, or cyclopropyl, cyclohexyl or cyclohexenyl which are unsubstituted, or cyclopropyl which is monosubstituted or disubstituted by identical or different substituents from the series comprising chlorine and methyl, or heterocyclic rings of the formula

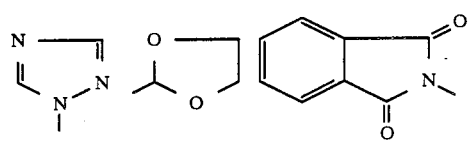

-continued

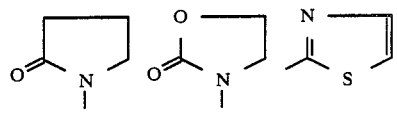

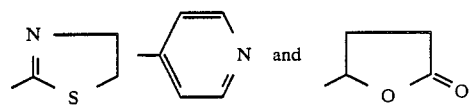

which are unsubstituted or monosubstituted to trisubstituted by methyl,
R¹ furthermore represents allyl, phenylallyl, propargyl, cyclohexyl or cyclohexenyl,
R² represents hydrogen, or alkyl which has 1 to 4 carbon atoms and which is straight-chain or branched, or alkylcarbonyl which has 1 to 3 carbon atoms in the straight-chain or branched alkyl moiety, or alkylaminocarbonyl which has 1 or 2 carbon atoms in the alkyl moiety, or represents straight-chain or branched alkyl which has 1 to 3 carbon atoms and which is monosubstituted by alkoxy or alkoxycarbonyl having 1 to 3 carbon atoms in the alkoxy moiety, cyano, hydroxyl, aminocarbonyl, phenyl, —COOH, phenylcarbonyl, cyclopropyl, triazolyl or dioxolanyl, halogenoalkyl which has 1 to 3 carbon atoms and 1 to 5 identical or different halogen atoms, such as fluorine or chlorine, or phenylsulphonyl, phenyl or phenyl which is monosubstituted to trisubstituted by identical or different substituents from the series comprising chlorine and methyl, or alkylthiocarbonyl which has 1 to 3 carbon atoms in the straight-chain or branched alkylthio moiety, or alkenyl or alkinyl, each of which has 3 or 4 carbon atoms,
R³ to R⁶ have the abovementioned meanings, and
R⁶ in the definition of OR⁶ in R¹ and of COR⁶ in R² can be identical or different in these two cases.

All aliphatic radicals as such or in compositions can be straight-chain or branched, even when it is not expressly stated.

The following 3-amino-2-pyrazolin-5-one derivatives of the general formula (I) may be mentioned individually in addition to the compounds mentioned in the preparation examples:

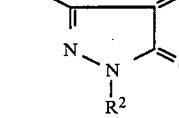 (I)

TABLE 1

| R¹ | R² | R¹ | R² |
|---|---|---|---|
| 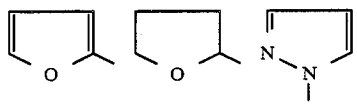 | H | 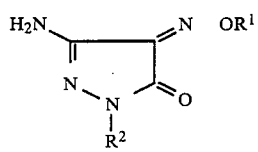 | H |

TABLE 1-continued
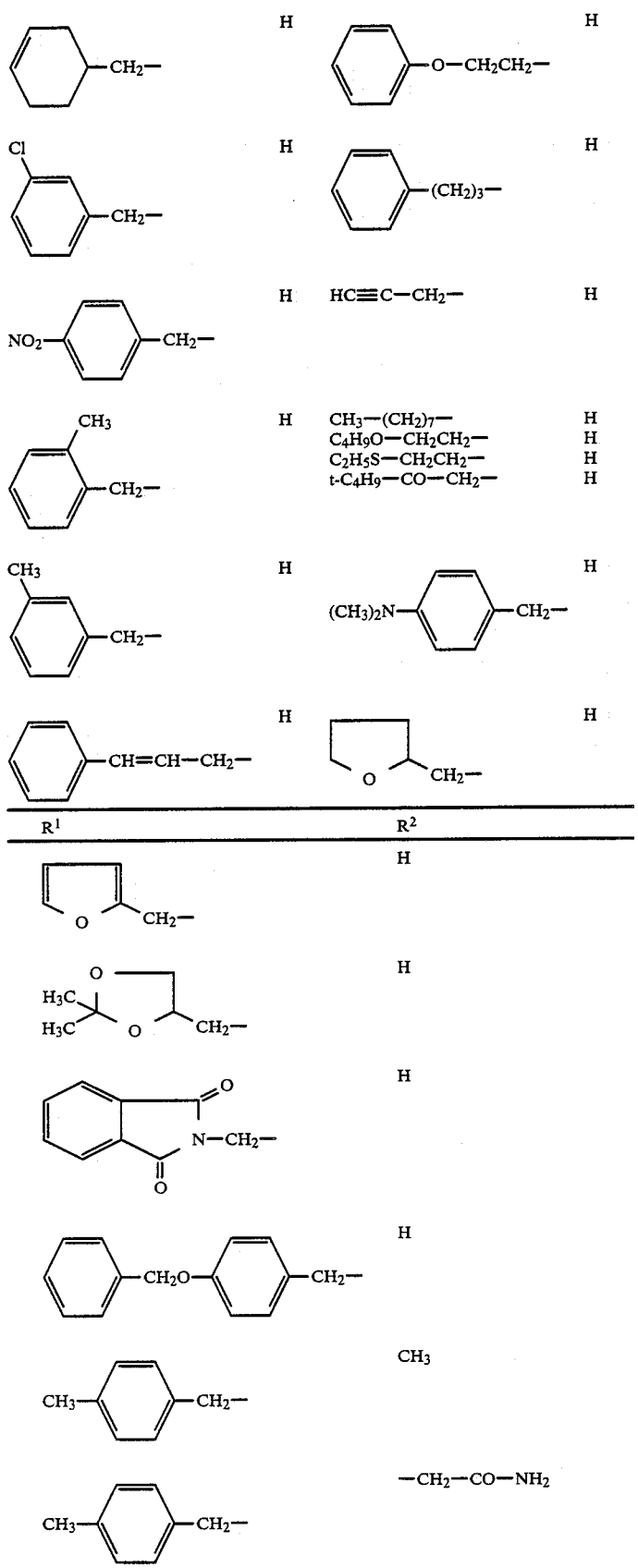

TABLE 1-continued

| | |
|---|---|
| CH₃—⟨C₆H₄⟩—CH₂— | —CH₂—CN |
| CH₃—⟨C₆H₄⟩—CH₂— | —CH₂—CH₂—OH |
| CH₃—⟨C₆H₄⟩—CH₂— | —CH₂—C₆H₅ |
| CH₃—⟨C₆H₄⟩—CH₂— | —CH₂—CH=CH₂ |
| CH₃—⟨C₆H₄⟩—CH₂— | —COOCH₃ |
| CH₃—⟨C₆H₄⟩—CH₂— | —SO₂—N(CH₃)₂ |
| CH₃—⟨C₆H₄⟩—CH₂— | —CO—SC₂H₅ |
| CH₃—⟨C₆H₄⟩—CH₂— | —CH₂—COOH |
| cyclohexyl- | H |
| —CH₂—S—CH₃ | H |
| —CH₂—CO—C₆H₅ | H |
| —CH₂—CO—C₆H₄—Br | H |
| —CH₂—cyclopropyl | H |
| —CH₂—C₆H₄—CF₃ | H |
| —CH₂—CH₂—N(CH₃)₂ | H |

TABLE 1-continued
| | |
|---|---|
| —CH₂CH₂—O—CH₂—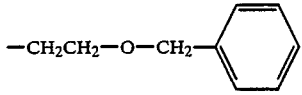 | H |
| 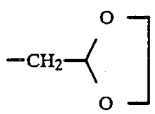 | H |
| 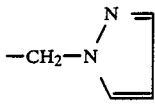 | H |
| 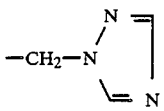 | H |
| 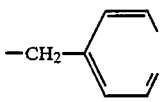 | H |
| 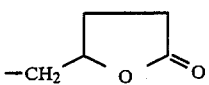 | H |
| 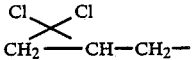 | H |
| —CH₂—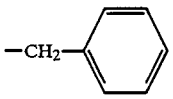 | —C₂H₅ |
| —CH₂—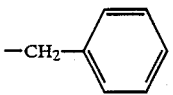 | —CH₂—CCl₃ |
| —CH₂—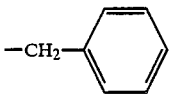 | —CH₂—CF₃ |
| —CH₂—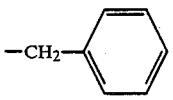 | —SO₂—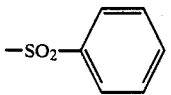 |
| —CH₂—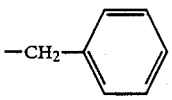 | —CH₂—O—CH₃ |
| —CH₂—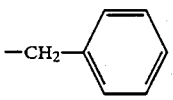 | —CH₂—CO—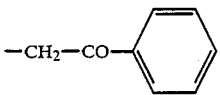 |
| —CH₂—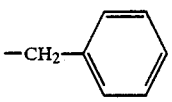 | —CH₂—CO—CH₃ |

TABLE 1-continued

| | |
|---|---|
| —CH₂—C₆H₅ | —CH₂—cyclopropyl |
| —CH₂—C₆H₅ | —CH₂—(1,3-dioxolan-2-yl) |
| —CH₂—C₆H₅ | —CH₂—N(N=CH—N=) (1,2,4-triazol-1-yl) |
| —CH₂—C₆H₅ | —CH₂—C≡CH |
| —CH₂—C₆H₅ | cyclohexyl—H |
| —CH₂—C₆H₅ | 4-Cl-C₆H₄— |
| —CH₂—C₆H₅ | cyclopentylmethyl-SO₂ |
| —CH₂—C₆H₅ | —CO—C₆H₅ |
| —CHF₂ | H |
| —CH₂—CN | H |
| —CH₂—COOH | H |
| —CH₂—CO—NH₂ | H |
| —CH₂—CO—N(C₂H₅)₂ | H |
| —CH₂—CO—NH—C₆H₅ | H |
| —CH₂—O—CH₃ | H |

If, for example, (E)-2-benzyloximino-2-cyanoacetyl chloride and methylhydrazine are used as the starting materials, triethylamine as the base and 4-dimethylaminopyridine as the catalyst, the course of the reaction of process (a) according to the invention may be represented by the following equation:

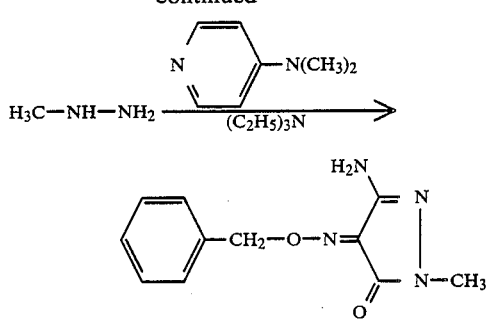

If, for example, (E)-3-amino-4-benzyloximino-2-pyrazolin-5-one and methyl isocyanate are used as the starting materials and triethylamine as the base, the course of the reaction of process (b3) according to the invention may be represented by the following equation:

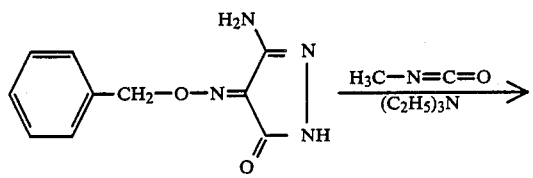

If, for example, the sodium salt of (E)-3-amino-4-hydroximino-2-pyrazolin-5-one and ethyl bromoacetate are used as the starting materials, the course of the reaction of process (c) may be represented by the following equation:

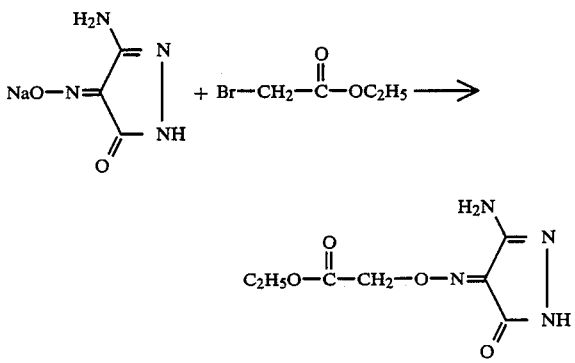

Formula (II) provides a general definition of the 2-cyano-2-oximino-acetic acid derivatives required as starting materials for carrying out process (a) according to the invention. In this formula (II), $R^1$ preferably represents the meaning which has already been mentioned in the description of the substances of the formula (I) according to the invention as being preferred for this substituent. $R^8$ preferably represents methoxy, ethoxy or chlorine.

The compounds of the formula (II) are known (cf. in this connection, for example, DE-OS (German Published Specification) No. 3,719,226), or they can be obtained by the processes described therein.

Formula (III) provides a general definition of the hydrazines also to be used as starting materials for carrying out process (a) according to the invention.

In this formula (III), $R^2$ has the meanings which have already been mentioned in connection with the description of the substances of the formula (I) according to the invention as being preferred for this substituent.

The hydrazines of the formula (III) are generally known compounds of organic chemistry.

Suitable diluents for carrying out process (a) according to the invention are organic solvents or aqueous systems.

These include, in particular, aliphatic or aromatic, optionally halogenated hydrocarbons, such as, for example, benzine, benzene, toluene, xylene, chlorobenzene, petroleum ether, hexane, cyclohexane, dichloromethane, chloroform or carbon tetrachloride; ethers, such as diethyl ether, dioxane, tetrahydrofuran or ethylene glycol dimethyl ether or ethylene glycol diethyl ether; alcohols, such as methanol or ethanol; nitriles, such as acetonitrile or propionitrile; amides, such as dimethylformamide, dimethylacetamide, N-methylformanilide, N-methylpyrrolidone or hexamethylphosphoric triamide, and also water or aqueous/organic two-phase mixtures, such as dichloromethane/water or toluene/water.

If appropriate, process (a) according to the invention is carried out in the presence of an acid-binding agent.

Suitable acid-binding agents are all customary inorganic or organic bases. These include, for example, alkali metal carbonates, such as sodium carbonate, potassium carbonate or sodium hydrogen carbonate, as well as tertiary amines, such as triethylamine, N,N-dimethylaniline and pyridine.

If appropriate, process (a) according to the invention is carried out in the presence of a catalyst. Examples which may be mentioned are tertiary amines, such as N,N-dimethylaminopyridine, diazabicyclooctane (DABCO), diazabicyclononene (DBN) or diazabicycloundecene (DBU).

When carrying out process (a) according to the invention, the reaction temperatures can be varied within a substantial range. In general, the process is carried out at temperatures between $-20°$ C. and $+160°$ C., preferably at temperatures between $0°$ C. and $+120°$ C.

When carrying out process (a) according to the invention, 1.0 to 3.0 moles, preferably 1.0 to 2.0 moles, of hydrazine of the formula (III), if appropriate 1.0 to 3.0 moles, preferably 1.0 to 2.0 moles, of a base, and if appropriate 0.001 to 1.0 mole, preferably 0.01 to 0.2 mole, of a catalyst are generally employed per mole of 2-cyano-2-oximino-acetic acid derivative of the formula (II).

The reaction is carried out and the reaction products of the formula (I) are worked up and isolated in a generally customary manner.

Formula (Ia) provides a general definition of the 4-oximino-2-pyrazolin-5-one derivatives required as starting materials for carrying out the process variants (b) according to the invention. In this formula (Ia), $R^1$ preferably represents those meanings which have already been mentioned in the description of the substances of the formula (I) according to the invention as being preferred for this substituent.

The compounds of the formula (Ia) are compounds according to the invention and can be obtained by processes (a) and (c). Formula (IV) provides a general definition of the alkylating agents furthermore required as starting materials for carrying out process (b1) according to the invention. In this formula (IV), $R^{2-1}$ represents the radicals mentioned under the formula (IV) and the corresponding parts of definitions which have already been mentioned in the description of the substances of the formula (I) according to the invention as being preferred and particular preferred for these substituents. A preferably represents halogen, in particular chlorine, bromine or iodine, or represents unsubstituted or substituted alkylsulphonyloxy, alkoxysulphonyloxy or arylsulphonyloxy, such as, for example, methanesulphonyloxy, methoxysulphonyloxy, trifluoromethanesulphonyloxy or p-toluenesulphonyloxy.

The alkylating agents of the formula (IV) are generally known compounds of organic chemistry.

Formulae (Va) and (Vb) provide general definitions of the acylating reagents also to be used as starting materials for carrying out process variants (b2) and (b3) according to the invention. In formula (Va), Z preferably represents a leaving group. These preferably include chlorine, bromine and alkoxy and alkylthio, in each case having 1 to 4 carbon atoms, carboxymethoxy, carboxymethylthio and the groups $-O-CO-R^{2-2}$, $-O-CO-OR^{2-1}$, $-OR^{2-1}$ and $-SR^{2-1}$. In this context, $R^{2-2}$ and $R^{2-1}$ preferably have the meanings which have already been mentioned in connection with the formulae (Va) and (IV) and with the description of the substances of the formula (I) according to the invention as being preferred for the corresponding parts of the definitions of the substituents.

In formula (Vb), X and $R^{2-3}$ preferably have the meanings which have already been mentioned in connection with the formula (Vb) and with the description of the substances of the formula (I) according to the invention as being preferred for the corresponding parts of the definitions of the substituents.

The acylating reagents of the formulae (Va) and (Vb), that is to say, carboxylic acid halides, carboxylic acid anhydrides, halogenoformic acid esters and halogenoformic acid thiol esters, trithiocarbonates, pyrocarbonates, carbamic acid halides, carbamates, thiolcarbamates, dithiocarbamates, isocyanates or isothiocyanates, are generally known compounds of organic chemistry and can be obtained by generally customary methods.

Suitable diluents for process (b) according to the invention are inert aprotic organic solvents. These preferably include ethers, tetrahydrofuran or 1,2-dimethoxyethane, nitriles, such as acetonitrile, amides, such as dimethylformamide or N-methylpyrrolidone, sulphoxides, such as dimethyl sulphoxide, esters, such as ethyl acetate, or aqueous-organic two-phase mixtures, such as water/toluene or water/dichloromethane.

If appropriate, the process variants (b) according to the invention are carried out in the presence of an acid-binding agent.

Suitable acid-binding agents are all customary inorganic or organic bases. These include, for example, alkali metal hydroxides, alkali metal amides, alkali metal alkoxides or alkali metal hydrides, such as sodium hydroxide or potassium hydroxide, sodium methoxide or Potassium t-butoxide, sodium hydride or sodium amide, alkali metal carbonates, such as sodium carbonate, potassium carbonate or sodium hydrogen carbonate, tertiary amines, such as triethylamine, N,N-dimethylaniline, pyridine, N,N-dimethylaminopyridine, diazabicyclooctane (DABCO), diazabicyclononene (DBN) or diazabicycloundecene (DBU), as well as organometal compounds, such as butyllithium and lithium diisopropylamide.

If appropriate, the process variants (b) according the invention are carried out in the presence of a catalyst. Examples which may be mentioned are tertiary amines, such as 4-dimethylaminopyridine, 1,8-diazabicyclo[5,4,-0]undec-7-ene (DBU) or 1,4-diazabicyclo-[2,2,2]-octane (DABCO); furthermore imidazole and dimethylformamide.

If the reactions are carried out in an organic-aqueous two-phase system, the process can be carried out, if appropriate, in the presence of 0.1 to 1 mole of a suitable phase transfer catalyst, such as, for example, a quaternary ammonium or phosphonium compound. Triethylbenzylammonium chloride and benzyl-dodecyl-dimethylammonium chloride may be mentioned by way of example.

When carrying out process variants (b1)–(b3) according to the invention, 1.0 to 1.5 moles, preferably 1.0 to 1.1 moles, of alkylating agents of the formula (IV), or 1.0 to 1.5 moles, preferably 1.0 to 1.1, moles of acylating agents of the formulae (Va) or (Vb), and if appropriate 1.0 to 3.0 moles, preferably 1.0 to 1.5 moles, of a base, and if appropriate 0.001 to 1.0 mole, preferably 0.01 to 0.2 mole, of a catalyst are generally employed per mole of 4-alkoximino-2-pyrazolin-5-one derivative of the formula (Ia).

When carrying out process (b) according to the invention, the reaction temperatures can be varied within a substantial range. In general, the process is carried out between $-20°$ C. and $+120°$ C., preferably between $0°$ C. and $40°$ C.

The reaction products of the formula (I) are worked up and isolated by customary methods.

Formula (VI) provides a general definition of the 4-oximino-2-pyrazolin-5-one derivatives required as starting materials for carrying out process (c) according to the invention. In this formula (VI), M preferably represents hydrogen, or represents a sodium or potassium cation.

The 4-oximino-2-pyrazolin-5-one derivatives of the formula (VI) were hitherto unknown. However, they can be prepared in a known manner following process variant (a), for example by reacting alkali metal salts of the 2-cyano-2-oximino-acetic acid derivatives of the formula (IIa)

in which
M represents a lithium, sodium or potassium cation and
$R^9$ represents methyl or ethyl,
with hydrazine hydrate, of the formula (IIIa),

if appropriate in the presence of a diluent, if appropriate in the presence of a base and if appropriate in the presence of a catalyst.

The compounds of the formula (IIa) are known (cf., in this context, Liebigs. Ann. Chem. 1981, 1561).

Hydrazine hydrate, of the formula (IIIa), is a generally known compound of organic chemistry.

Formula (VII) provides a general definition of the alkylating agents furthermore required as starting materials for carrying out process (c) according to the invention. In this formula (VII), $R^1$ preferably represents those radicals which have already been mentioned in the description of the substances of the formula (I) according to the invention as being preferred for the substituents $R^1$.

A preferably represents those leaving groups which have already been mentioned in the description of the alkylating agents of the formula (IV) as being preferred for the substituent A.

The alkylating agents of the formula (VII) are likewise generally known compounds of organic chemistry.

Suitable diluents for carrying out process (c) according to the invention are organic solvents or aqueous systems.

These include, in particular, aromatic hydrocarbons, such as benzene, toluene or xylene; ethers, such as tetrahydrofuran, dioxane or dimethoxyethane; ketones, such as acetone or methyl isobutyl ketone; nitriles, such as acetonitrile; amides, such as dimethylformamide, or N-methylpyrrolidone; esters, such as ethyl acetate; sulphoxides, such as dimethyl sulphoxide; alcohols, such as methanol or ethanol, as well as water, mixtures of solvents with water, or mixtures of several solvents.

If the reaction is carried out in an organic-aqueous two-phase system, the reaction can be carried out, if appropriate, in the presence of 0.1 to 1 mole of a suitable phase transfer catalyst, such as, for example, in a quaternary ammonium or phosphonium compound. Triethylbenzylammonium chloride and benzyl-dodecyl-dimethylammonium chloride may be mentioned by way of example.

When carrying out process (c) according to the invention, the reaction temperatures can be varied within a substantial range. In general, the process is carried out at temperatures between $-20°$ C. and $+160°$ C., preferably at temperatures between $20°$ C. and $+100°$ C.

When carrying out process (c) according to the invention, the reactants are generally preferably employed in an equimolar ratio. However, under certain conditions it can be advantageous to employ an excess of one or the other component.

The reaction products of the formula (I) are worked up and isolated by customary methods.

The active compounds according to the invention show a powerful biological action and can be employed in practice for combating undesired pests. For example, the active compounds can be employed for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation:

Xanthomonas species, such as, for example, *Xanthomonas campestris pv. oryzae;* Pseudomonas species, such as, for example, *Pseudomonas syringae pv. lachrymans;* Erwinia species, such as, for example, *Erwinia amylovora;* Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example *Venturia inaequalis;* Pyrenophora species, such as, for example, *Pyrenophora teres* or *P. graminea* (conidia form: Drecnslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be employed with particularly good success protectively, for combating Pyricularia species in rice.

Moreover, some of the active compounds according to the invention also show a good action against Oomycetes.

Depending on their particular physical and/or chemical properties, the active compounds can be converted into the customary formulations, such as solutions, emulsions, suspensions, powders, foams, pastes, granules, aerosols, natural and synthetic substances impregnated with active compound, very fine capsules in polymeric substances and in coating compositions for seed, as well as ULV cold and warm mist formulations.

These formulations are produced in a known manner, for example by mixing the active compounds with extenders, that is, liquid solvents, liquefied gases under pressure and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates. As solid carriers for granules there are suitable:

for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming a there are suitable: for example non-ionic and an emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithin, and synthetic phospho-lipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The preparation and the use of the active compounds according to the invention can be seen from the examples below.

PREPARATION EXAMPLES

Example 1

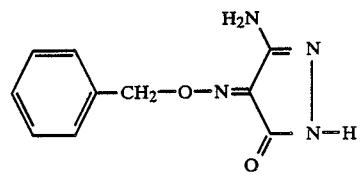

(Process a)

50 g (1 mol) of hydrazine hydrate are added dropwise to a solution of 150.2 g (0 5 mol) of 78% strength ethyl (E)-2-benzyloximino-2-cyano-acetate in 500 ml of ethanol, and the mixture is stirred for 15 hours at room temperature. The dark, reddish-brown precipitate is filtered off with suction, washed with ethanol and dried under reduced pressure at 50° C. This gives 71.6 g (60% of theory) of (E)-3-amino-4-benzyl-oximino-2-pyrazolin-5-one containing 92% of product (HPLC=high pressure liquid chromatography) and a melting point of 198°-201° C. (decomposition).

Preparation of the starting substances

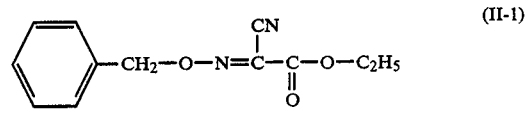

253.1 g (2 mol) of benzyl chloride are added dropwise to a suspension of 328.2 g (2 mol) of the sodium salt of ethyl (E)-2-cyano-2-hydroximino-acetate in 1500 ml of dimethyl sulphoxide, and mixture is stirred for 20 hours at 60° C. After 150 of water has been added, the mixture is extracted using ethyl acetate (3×500 ml), and the extract is washed with water (3×500 ml), dried over magnesium sulphate and concentrated under reduced pressure. This gives 374.5 g (63% of theory) of a reddish-brown oil containing 78% of ethyl (E)-2-benzyl-oximino-2-cyano-acetate.

$^1$H—NMR*): $\delta$=1.35 ppm (t, 3H); 4.35 (q, 2H); 5.45 (s, 2H); 7.35 (ar, 5H).

*) The $^1$H—NMR spectra were recorded in deuterochloroform (CDCl$_3$) with tetramethylsilane (TMS) as the internal standard. The chemical shift is indicated as $\delta$-value in ppm.

Example 2

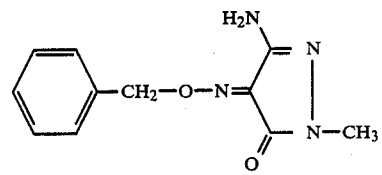

(Process a)

A solution of 17.8 g (0.08 mol) of (E)-2-benzyloximino-2-cyano-acetyl chloride in 100 ml of methylene chloride is added dropwise at 0° C. to a solution of 8.1 g (0.08 mol) of triethylamine, 0.98 g (0.008 mol) of 4-dimethylaminopyridine and 3.7 g (0.08 mol) of methylhydrazine in 200 ml of methylene chloride, and the mixture is stirred for 18 hours at room temperature. The reaction mixture is washed with 100 ml of water, dried over sodium sulphate and concentrated under reduced pressure. The residue is chromatographed on silica gel 60 using ethyl acetate.

This gives 8.9 g (48% of theory) of (E)-3-amino-4-benzyloximino-1-methyl-2-pyrazolin-5-one as a dark red solid of melting point 105°–108° C.

Preparation of the starting substance $$\text{C}_6\text{H}_5\text{—CH}_2\text{—O—N=C(CN)—C(=O)—Cl} \quad (\text{II-2})$$

2 drops of dimethylformamide are added to a suspension of 48.5 g (0.2 mol) of the potassium salt of (E)-2-benzyloximino-2-cyano-acetic acid in 200 ml of absolute ether, and 126.9 g (1.0 mol) of oxalyl chloride are added dropwise at 0° C. The mixture is subsequently stirred for 2 hours at 0° C. The reaction mixture is filtered over kieselguhr, the filtrate is concentrated at room temperature under reduced pressure, and the residue is evaporated twice under reduced pressure using 50 ml of methylene chloride each time.

This gives 40.2 g (90% of theory) of (E)-2-benzyloximino-2-cyano-acetyl chloride, which is immediately reacted further.

$$\text{C}_6\text{H}_5\text{—CH}_2\text{—O—N=C(CN)—C(=O)—OK}$$

A solution of 12.5 g (0 22 mol) of potassium hydroxide in 60 ml of ethanol is added dropwise at 20° to 30° C. to a solution of 59.5 g (0.2 mol) of 78% strength ethyl (E)-2-benzyloximino-2-cyano-acetate in 50 ml of ethanol, and the mixture is stirred for 1 hour at room temperature. The mixture is diluted with 100 ml of ether, and the precipitate is then filtered off with suction, washed with 100 ml of ether and dried under reduced pressure at room temperature.

This gives 41.2 g (85% of theory) of colorless potassium salt of (E)-2-benzyloximino-2-cyano-acetic acid, which undergoes vigorous decomposition at 166° C.

Example 3

(Process b2)

3.2 g (0.01 mol) of tetrabutylammonium bromide and 12.2 g (0.105 mol) of 97% strength potassium tert-butoxide are added at 20° C with stirring to a suspension of 23.7 g (0.1 mol) of 92% strength (E)-3-amino-4-benzyloximino-2-pyrazolin-5-one in 400 ml of absolute tetrahydrofuran. As soon as the mixture has become homogeneous, a solution of 18.4 g (0.11 mol) of ethyl bromoacetate in 50 ml of absolute tetrahydrofuran is added, and the mixture is stirred for 15 hours at room temperature. The reaction mixture is poured into 1 liter of water and extracted using ethyl acetate (3×500 ml), and the extract is washed with water (3×500 ml), dried and concentrated under reduced pressure. This gives 28.6 g (94% of theory) of reddish-brown (E)-3-amino-4-benzyloximino-1-ethoxycarbonylmethyl-2-pyrazolin-5one of melting point 102°–108° C.

Example 4

(Process b3)

3 drops of triethylamine are added to a suspension of 16.6 g (0.07 mol) of (E)-3-amino-4-benzyloximino-2-pyrazolin-5-one in 130 ml of dioxane, 4.0 g (0.07 mol) of methyl isocyanate are added dropwise to this, and the reaction mixture is stirred for 15 hours at 70° C. After the mixture has cooled, the precipitate is filtered off, washed with dioxane and dried under reduced pressure.

This gives 10.9 g (57% of theory) of reddish-brown (E)-3-amino-4-benzyloximino-1-methylcarbamoyl-2-pyrazolin-5-one of melting point 195°–203 C.

Example 5

(Process c)

15.0 g (0.1 mol) of the sodium salt of (E)-3-amino-4-hydroximino-2-pyrazolin-5-one stirred for 6 hours at 80° C. with 17.0 g (0.1 mol) 98% strength ethyl bromoacetate. The reaction mixture concentrated, and the residue is chromatographed on silica gel 60 using ethyl acetate. This gives 6.6 g (26% of theory) of (E)-3-amino-4-ethoxycarbonylmethoximino-2-pyrazolin-5-one containing 84% of product (HPLC) and having a melting point of 152°–158° C.

Preparation of the starting substance (VI-1)

164.1 g (1 mol) of the sodium salt of ethyl (E)-2-cyano-2-hydroximino-acetate are refluxed for 3 hours with 75 g (1.5 mol) of hydrazine hydrate in 1.5 liters of ethanol. After the mixture has been cooled to 5° C., the precipitate is filtered off with suction, washed with cold ethanol and dried under reduced pressure over Sicapent.

This gives 110 g (73% of theory) of the reddish-brown sodium salt of (E)-3-amino-4-hydroximino-2-pyrazolin-5-one, which undergoes decomposition at 280° C.

The end products of the formula (I) which are listed in Table 2 below are obtained analogously to the methods described in Examples 1 to 5 and with consideration of the instructions in the descriptions of the processes according to the invention:

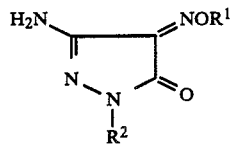

(I)

TABLE 2

| Example No. | R¹ | R² | Physical constant/m.p. |
|---|---|---|---|
| 6 | ⟨phenyl⟩—CH₂— | —C(=O)—CH₃ | 255–260° C. |
| 7 | CH₃— | H | 193–195° C. |
| 8 | 2-Cl-C₆H₄-CH₂— | H | >260° C. |
| 9 | 2-Cl-C₆H₄-CH₂— | CH₃— | amorphous |
| 10 | CH₃— | CH₃— | 126° C. |
| 11 | ⟨phenyl⟩—CH₂— | ⟨phenyl⟩— | 154–156° C. |
| 12 | Cl-C₆H₄-CH₂— | CH₃— | 163–165° C. |
| 13 | Cl,Cl-C₆H₃-CH₂— | H | >230° C. |
| 14 | Cl-C₆H₄-CH₂— | H | 230–233° C. |
| 15 | ⟨phenyl⟩—CH₂CH₂— | H | 195–199° C. |
| 16 | H₃C-C₆H₄-CH₂— | H | 219°–225° C. |
| 17 | CH₂=CH—CH₂— | H | 136–139° C. |
| 18 | Cl,Cl-C₆H₃-CH₂— | H | 193–196° C. |
| 19 | ⟨phenyl⟩—C(=O)—O—CH₂CH₂— | H | 178–180° C. |
| 20 | H₃CO-C₆H₄-CH₂— | H | 165–170° C. |

Use Example

In the use example which follows, the compounds listed below are employed as comparison substances:

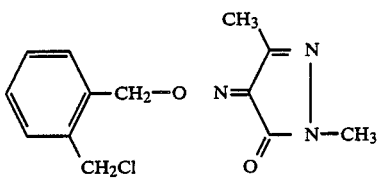

(A)

1,3-Dimethyl-4-(2-chloromethyl-benzyloximino)-2-pyrazolin-5-one

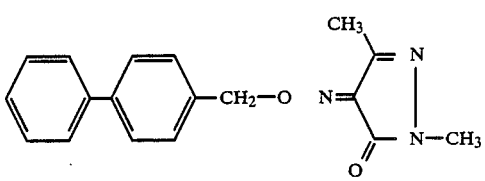

(B)

1,3-Dimethyl-4-(4-phenyl-benzyloximino)-2-pyrazolin-5-one

[The compounds (A) and (B) are known from EP-OS (European Published Specification) No. 0,166,171]

Example A

Pyricularia test (rice)/protective

| Solvent: | 12.5 | parts by weight of acetone |
|---|---|---|
| Emulsifier: | 0.3 | part by weight of alkylaryl polyglycol ether |

To produce a suitable preparation of active compound, 1 part by weight of active compound is mixed with the stated amount of solvent, and the concentrate is diluted with water and the stated amount of emulsifier to the desired concentration.

To test for protective activity, young rice until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, a higher degree of effectiveness than comparison substances (A) and (B) is shown at an active compound concentration of 0.025% by weight in the spray liquor by the active compounds according to the invention, Examples 2, 3, 6, 11, 14, 15 and 16.

It will be appreciated that the instant specification and claims are set forth by way of illustration and not limitation, and that various modifications and changes may be made without departing from the spirit and scope of the present invention.

What is claimed is:

1. A substituted 3-amino-2-pyrazolin-5-one derivative of the formula

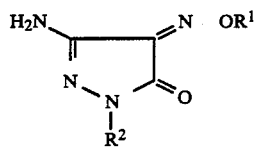 (I)

in which
R[1] represents unsubstituted or substituted alkyl, unsubstituted or substituted alkenyl or alkinyl, or unsubstituted or substituted cycloalkyl or cycloalkenyl,
R[2] represents hydrogen, unsubstituted or substituted alkyl, unsubstituted or substituted alkenyl or alkinyl, unsubstituted or substituted cycloalkyl or cycloalkenyl, unsubstituted or substituted aryl or unsubstituted or substituted 6-membered heterocyclyl, or represents one of the radicals
—CX—YR[3], —CXNR[4]R[5],

—SO$_2$NR[4]R[5] or —SO$_2$R[7],
R[3] represents unsubstituted or substituted alkyl or unsubstituted or substituted alkenyl or alkinyl,
R[4] and R[5] are identical or different and represent hydrogen, unsubstituted or substituted alkyl, unsubstituted or substituted alkenyl or alkinyl or unsubstituted or substituted aryl or 6-membered heterocyclyl, or together with the nitrogen atom which they are bonded represent an unsubstituted or substituted 6-membered heterocyclic ring which can contain further hetero atoms,
R[6] represents hydrogen, unsubstituted or substituted alkyl, unsubstituted or substituted alkenyl or alkinyl, unsubstituted or substituted cycloalkyl or cycloalkenyl, unsubstituted or substituted aryl or unsubstituted or substituted 6-membered heterocyclyl alkoxycarbonyl or phenylcarbonyl,
R[7] represents unsubstituted or substituted alkyl or unsubstituted or substituted aryl and
X and Y are identical or different and represent oxygen or sulphur.

2. A substituted 3-amino-2-pyrazolin-5-one derivative according to claim 1, in which
R[1] represents straight-chain or branched alkyl which has 1 to 10 carbon atoms and which is unsubstituted or monosubstituted to pentasubstituted by identical or different substituents, selected from the group consisting of fluorine, chlorine, bromine, iodine, cyano, —COOH, —COOR[3], —CONR[4]R[5], —OR[6], —SR[6], alkylcarbonyl having 1 to 9 carbon atoms, phenylcarbonyl which is unsubstituted or monosubstituted to trisubstituted by identical or different halogen substituents, phenyl which is unsubstituted or monosubstituted to pentasubstituted by identical or different substituents selected from the group consisting of halogen, nitro, alkyl and alkoxy, each having 1 to 4 carbon , halogenoalkyl and halogenoalkoxy, each 1 or 2 carbon atoms and 1 to 5 identical or halogen atoms; amino, alkylamino and dialkylamino, each having 1 to 4 carbon atoms in the individual alkyl moieties, aryloxy and aralkoxy, each having 6 to 12 carbon atoms in the aryl moiety and 1 to 4 carbon atoms in the alkoxy moiety; further optional substituents on alkyl are cycloalkyl or cycloalkenyl which have 3 to 6 carbon atoms and which are unsubstituted or monosubstituted to pentasubstituted by identical or different substituents from the group consisting of chlorine and alkyl having 1 to 4 carbon atoms, and 6-membered heterocyclyl which has 1 to 3 identical or different hetero atoms, and which is unsubstituted or monosubstituted to pentasubstituted by identical or different substituents from the group consisting of halogen, hydroxyl, oxo, alkyl and alkoxy having 1 to 4 carbon atoms; R[1] furthermore represents straight-chain or branched alkenyl or alkinyl, each of which has 2 to 6 carbon atoms and each of which is unsubstituted or monosubstituted to trisubstituted by identical or different substituents selected from the group consisting of phenyl which is unsubstituted or monosubstituted to pentasubstituted by identical or different substituents from the group consisting of halogen, and alkyl and alkoxy having 1 to 4 carbon atoms; R[1] furthermore represents cycloalkyl which has 3 to 6 carbon atoms or cycloalkenyl which has 5 to 7 carbon atoms, each of these radicals being unsubstituted or monosubstituted to pentasubstituted by identical or different substituents from the group consisting of chlorine, and alkyl and alkoxy having 1 to 4 carbon atoms;
R[2] represents hydrogen, or represents straight-chain or branched alkyl which has 1 to 6 carbon atoms and which is unsubstituted or monosubstituted to pentasubstituted by identical or different substituents selected from the group consisting of fluorine, chlorine, bromine, iodine, cyano, —COOH, —COOR[3], —CONR[4]R[5], —OR[6], —SR[6], alkylcarbonyl having 1 to 9 carbon atoms, phenylcarbonyl which is unsubstituted or monosubstituted to trisubstituted by identical or different halogen substituents, and phenyl which is unsubstituted or monosubstituted to pentasubstituted by identical or different substituents selected from the group consisting of halogen, nitro, alkyl and alkoxy, each having 1 to 4 carbon atoms, halogenoalkyl and halogenoalkoxy each having 1 or 2 carbon atoms and 1 to 5 identical or different halogen atoms, amino, alkylamino and dialkylamino each having 1 to 4 carbon atoms in the individual alkyl moieties, and aryloxy and aralkoxy each having 6 to 12 carbon atoms in the aryl moiety and 1 to 4 carbon atoms in the alkoxy moiety; further alkyl substituents are cycloalkyl which has 3 to 6 carbon atoms and which is unsubstituted or monosubstituted to pentasubstituted by identical or different substituents from the group consisting of chlorine and alkyl having 1 to 4 carbon atoms, 6-membered heterocyclyl which has 1 to 3 identical or different hetero atoms and which is unsubstituted or monosubstituted to pentasubstituted by identical or different substituents from the group consisting of halogen, hydroxyl, oxo, alkyl and alkoxy having 1 to 4 carbon atoms; R[2] furthermore represents straight-chain or branched alkenyl or alkinyl, each of which has 2 to 6 carbon atoms and each of which is unsubstituted or monosubstituted to trisubstituted by identical or different substituents selected from the group consisting of phenyl which is unsubstituted or monosubstituted to pentasubstituted by identical or different substituents from the group consisting of halogen and alkyl having 1 to 4 carbon atoms; R[2]

furthermore represents cycloalkyl which has 3 to 6 carbon atoms or cycloalkenyl which has 5 to 7 carbon atoms, each of these radicals being unsubstituted or monosubstituted to pentasubstituted by identical or different alkyl substituents having 1 to 4 carbon atoms: $R^2$ furthermore represents aryl which has 6 to 12 carbon atoms and which is unsubstituted or monosubstituted to pentasubstituted by identical or different substituents selected from the group consisting of halogen, nitro, alkyl or alkoxy each having 1 to 4 carbon atoms, and halogenoalkyl or halogenoalkoxy each having 1 or 2 carbon atoms in the alkyl moiety and 1 to 5 identical or different halogen atoms; or $R^2$ furthermore represents 6-membered heterocyclyl which has 1 to 3 identical or different hetero atoms, and which is unsubstituted or monosubstituted to pentasubstituted by identical or different substituents from the group consisting of halogen, hydroxyl, oxo, and alkyl and alkoxy each having 1 to 4 carbon atoms, or represents one of the radicals $-CX-YR^3$, $-CXNR^4R^6$, $-CO-R^6$, $-SO_2-NR^4R^5$ or $-SO_2R^7$, where X and Y are identical or different and represent oxygen or sulphur, $R^3$ represents straight-chain or branched alkyl which has 1 to 6 carbon atoms and which is unsubstituted or monosubstituted to pentasubstituted by identical or different substituents selected from the group consisting of halogen, phenyl which is unsubstituted or monosubstituted to pentasubstituted by identical or different substituents selected from the group consisting of halogen, nitro, alkyl and alkoxy each having 1 to 4 carbon atoms, and halogenoalkyl or halogenoalkoxy each having 1 or 2 carbon atoms and 1 to 5 identical or different halogen atoms, and amino, alkylamino and dialkylamino each having 1 to 4 carbons in the individual alkyl moieties, and aryloxy and aralkoxy each having 6 to 12 carbon atoms in the aryl moiety and 1 to 4 carbon atoms in the alkoxy moiety, and furthermore represents cycloalkyl or cycloalkenyl in each case having 3 to 6 carbon atoms; or $R^3$ furthermore represents straight-chain or branched alkenyl or alkinyl each having 3 to 6 carbon atoms, $R^4$ and $R^5$ in each case are identical or different and represent hydrogen or represent alkyl which has 1 to 6 carbon atoms and which is unsubstituted or monosubstituted or disubstituted by identical or different substituents selected from the group consisting of alkoxy having 1 to 4 carbon atoms, phenyl which is unsubstituted or monosubstituted to pentasubstituted by identical or different substituents from the group consisting of halogen, nitro and alkyl and alkoxy each having 1 to 4 carbon atoms, or halogenoalkyl and halogenoalkoxy each having 1 or 2 carbon atoms and 1 to 5 identical or different halogen atoms, or amino, or alkylamino and dialkylamino each having 1 to 4 carbon atoms in the individual alkyl moieties, or aryloxy and aralkoxy, each having 6 to 12 carbon atoms in the aryl moiety and 1 to 4 carbon atoms in the alkoxy moiety, or represent cycloalkyl or cycloalkenyl, each of which has 3 to 6 carbon atoms, $R^4$ and $R^5$ furthermore represent alkenyl or alkinyl each of which has 3 to 6 carbon atoms, or represent phenyl which is unsubstituted or monosubstituted to pentasubstituted by identical or different substituents as mentioned above in the case of $R^4$ and $R^5$ as phenyl substituents, or represent 6-membered heterocyclyl which has 1 to 3 identical or different hetero atoms, and which is monosubstituted to trisubstituted by identical or different substituents selected from the group consisting of halogen, hydroxyl, alkyl and alkoxy each having 1 to 4 carbon atoms, and oxo; furthermore, $R^4$ and $R^5$ together with the nitrogen atom to which they are bonded represent a 6-membered heterocyclic ring which can contain 1 or 2 further identical or different hetero atoms, and which is unsubstituted or monosubstituted to trisubstituted by identical or different substituents selected from the group consisting of halogen, hydroxyl, alkyl and alkoxy each having 1 to 4 carbon atoms, and oxo, $R^6$ represents hydrogen or represents straight-chain or branched alkyl which has 1 to 6 carbon atoms and which is unsubstituted or monosubstituted to pentasubstituted by identical or different substituents selected from the group consisting of halogen, alkoxy having 1 to 4 carbon atoms, cycloalkyl which has 3 to 6 carbon atoms and which is unsubstituted or substituted, phenyl which is unsubstituted or monosubstituted to trisubstituted as mentioned above in the case of $R^4$ and $R^5$ as phenyl substituents; $R^6$ furthermore represents alkenyl or alkinyl each of which has 2 to 6 carbon atoms, cycloalkyl which has 3 to 6 carbon atoms, phenyl which is unsubstituted or monosubstituted to trisubstituted by identical or different substituents as mentioned above in the case of $R^4$ and $R^5$ as phenyl substituents, or 6-membered heterocyclyl which has 1 to 3 identical or different hetero atoms, and which is unsubstituted or monosubstituted to trisubstituted by identical or different substituents selected from the group consisting of halogen, hydroxyl, alkyl or alkoxy each having 1 to 4 carbon atoms, and oxo, or furthermore represents alkoxycarbonyl which has 1 or 2 carbon atoms, $R^7$ R represents alkyl which has 1 to 6 carbon atoms and which is unsubstituted or monosubstituted to pentasubstituted by chlorine, or represents phenyl which is unsubstituted or monosubstituted to trisubstituted by identical or different substituents as mentioned above in the case of $R^4$ and $R^5$ as phenyl substituents.

3. A substituted 3-amino-2-pyrazolin-5-one derivative according to claim 1, in which $R^1$ represents unsubstituted alkyl which has 1 to 8 carbon atoms, or represents straight-chain or branched alkyl which has 1 to 5 carbon atoms and which is monosubstituted to trisubstituted by identical or different substituents selected from the group consisting of fluorine, chlorine, bromine, iodine, cyano, $-COOH$, $-COOR^3$, $-CONR^4R^5$, $-OR^6$, $-SR^6$, alkylcarbonyl having 1 to 7 carbon atoms, phenylcarbonyl which is unsubstituted or monosubstituted or disubstituted by halogen, and phenyl which is unsubstituted or monosubstituted to trisubstituted by identical or different substituents from the group consisting of fluorine, chlorine, nitro, methyl, methoxy, trifluoromethyl, trifluoromethoxy, amino, methylamino, dimethylamino, phenyloxy and phenylmethoxy, and further alkyl substituents are cyclopropyl, cyclopentyl, cyclohexyl, cyclopentenyl or cyclohexenyl, each of which is unsubstituted or monosubstituted to trisubstituted by methyl or chlorine, and heterocyclic rings of the formulae

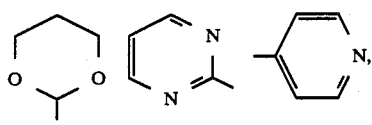

which are unsubstituted or monosubstituted to trisubstituted by identical or different substituents from the group consisting of fluorine, chlorine, methyl, methoxy or hydroxyl, or $R^1$ furthermore represents allyl or propargyl, each of which is optionally monosubstituted or disubstituted by phenyl which is unsubstituted or monosubstituted to trisubstituted by identical or different substituents from the group consisting of fluorine, chlorine, methyl and methoxy; or $R^1$ furthermore represents cyclopropyl, cyclopentyl, cyclohexyl, cyclopentenyl or cyclohexenyl, each of which is unsubstituted or monosubstituted to trisubstituted by chlorine, methyl or methoxy;

$R^2$ represents hydrogen, or represents straight-chain or branched alkyl which has 1 to 4 carbon atoms and which is unsubstituted or monosubstituted to trisubstituted by identical or different substituents selected from the group consisting of fluorine, chlorine, bromine, iodine, cyano, —COOH, —COOR$^3$, —CONR$^4$R$^5$, —OR$^6$, —SR$^6$, alkylcarbonyl having 1 to 7 carbon atoms, phenylcarbonyl which is unsubstituted or monosubstituted to trisubstituted by identical or different halogen substituents, and phenyl which is unsubstituted or monosubstituted to trisubstituted by identical or different substituents from the group consisting of fluorine, chlorine, nitro, methyl, methoxy, trifluoromethyl, trifluoromethoxy, amino, methylamino, dimethylamino, phenyloxy and phenylalkoxy having 1 or 2 carbon atoms in the alkoxy moiety; further alkyl substituents are cyclopropyl, cyclopentyl, cyclohexyl, cyclopentenyl or cyclohexenyl, each of which is unsubstituted or monosubstituted to trisubstituted by methyl or chlorine, or heterocyclic rings of the formulae

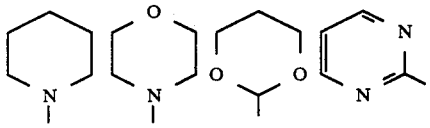

which are unsubstituted or monosubstituted to trisubstituted by identical or different substituents from the group consisting of fluorine, chlorine, methyl, methoxy and hydroxyl, $R^2$ furthermore represents allyl or propargyl, each of which is monosubstituted or disubstituted by identical or different substituents selected from the group consisting of phenyl which is unsubstituted or monosubstituted to trisubstituted by identical or different substituents from the group consisting of fluorine, chlorine, methyl and methoxy; $R^2$ furthermore represents cyclopropyl, cyclopentyl, cyclohexyl, cyclopentenyl or cyclohexenyl, each of which is unsubstituted or monosubstituted to trisubstituted by methyl or methoxy;

$R^2$ furthermore represents phenyl which is unsubstituted or monosubstituted to trisubstituted by identical or different substituents selected from the croup consisting of fluorine, chlorine, nitro, methyl, methoxy, trifluoromethyl and trifluoromethoxy, $R^2$ furthermore represents heterocyclic rings of the formulae

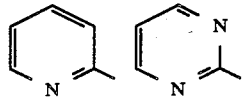

which are unsubstituted or monosubstituted to trisubstituted by identical or different substituents from the group consisting of fluorine, chlorine, hydroxyl, oxo, methyl and methoxy, or represents one of the radicals —CX—YR$^3$, —CXNR$^4$R$^5$, —COR$^6$, —SO$_2$—NR$^4$R$^5$ or —SO$_2$R$^7$, where X and Y are identical or different and represent oxygen or sulphur, $R^3$ represents straight-chain or branched alkyl which has 1 to 4 carbon atoms and which is unsubstituted or monosubstituted to trisubstituted by identical or different substituents selected from the croup consisting of fluorine, chlorine, bromine, iodine, phenyl which is unsubstituted or monosubstituted to trisubstituted by identical or different substituents from the group consisting of fluorine, chlorine, nitro, methyl, methoxy, trifluoromethyl, trifluoromethoxy, amino, methylamino, dimethylamino, phenyloxy and phenylalkoxy having 1 or 2 carbon atoms in the alkyl moiety, and cyploroyl, cyclopentyl, cyclohexyl, cyclopentenyl and cyclohexenyl, each of which is unsubstituted or monosubstituted to trisubstituted by methyl; $R^3$ furthermore represents allyl or propargyl, $R^4$ and $R^5$ are identical or different and represent hydrogen, or represent alkyl which has 1 to 4 carbon atoms and which is unsubstituted or monosubstituted or disubstituted by identical or different substituents selected from the group consisting of methoxy, ethoxy, phenyl which is unsubstituted or monosubstituted to trisubstituted by identical or different substituents from the group consisting of fluorine, chlorine, bromine, iodine, nitro, methyl, methoxy, trifluoromethyl, trifluoromethoxy, amino, methylamino, dimethylamino, phenoxy and phenylmethoxy;

$R^4$ and $R^5$ furthermore represent allyl, propargyl, cyclopropyl, cyclopentyl, cyclohexyl, cyclopentenyl, cyclohexenyl and phenyl which is unsubstituted or monosubstituted to trisubstituted by identical or different substituents, suitable phenyl substituents being the substituents mentioned above in the cases of $R^4$ and $R^5$ as phenyl substituents, or furthermore represent heterocyclic rings of the formulae

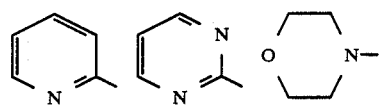

-continued

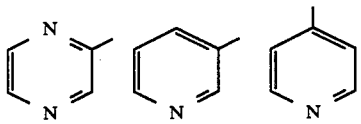

which are monosubstituted to trisubstituted by identical or different substituents from the group consisting of fluorine, chlorine, methyl, methoxy, hydroxyl and oxo, or $R^4$ and $R^5$ together with the nitrogen atom to which they are bonded represent piperazine, morpholine, thiomorpholine, 1,3-oxazane or 1,3-diazane, each of which is unsubstituted or substituted by fluorine, chlorine, bromine, iodine, hydroxyl, methyl, methoxy or oxo, $R^6$ represents hydrogen, or represents straight-chain or branched alkyl which has 1 to 4 carbon atoms and which is unsubstituted or monosubstituted to trisubstituted by identical or different substituents from the group consisting of fluorine, chlorine, bromine, iodine, methoxy, cyclopropyl, cyclopentyl, cyclohexyl, phenyl which is unsubstituted or monosubstituted or disubstituted by identical or different substituents as mentioned above in the cases of $R^4$ and $R^5$ as phenyl substituents; furthermore represents allyl or propargyl, cyclopropyl, cyclopentyl or cyclohexyl, or represents phenyl which is unsubstituted or monosubstituted or di-substituted by identical or different substituents as mentioned above in the cases of $R^4$ and $R^5$ as phenyl substituents; furthermore represents heterocyclic rings of the formulae

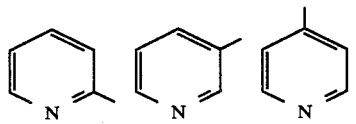

which are unsubstituted or monosubstituted to trisubstituted by identical or different substituents from group consisting of fluorine, chlorine, bromine, iodine, hydroxyl, oxo, methyl and methoxy, and furthermore represents methoxycarbonyl or ethoxycarbonyl or phenylcarbonyl, $R^7$ represents alkyl which has 1 to 4 carbon atoms and which is unsubstituted or monosubstituted to trisubstituted by chlorine, or represents phenyl which is unsubstituted or monosubstituted to trisubstituted by identical or different substituents as mentioned above in the cases of $R^4$ and $R^5$ as phenyl substituents.

4. A substituted 3-amino-2-pyrazolin-5-one derivative according to Claim 1, in which $R^1$ represents unsubstituted alkyl which has 1 to 8 carbon atoms, or represents methyl, ethyl or n- or i-propyl, each of which is monosubstituted or disubstituted by identical or different substituents selected from the group consisting of fluorine, cyano, —COOH, —COOR$^3$, —CONR$^4$R$^5$, —OR$^6$, —SR$^6$, alkylcarbonyl which has 1 to 5 carbon atoms, phenylcarbonyl which is unsubstituted or monosubstituted or disubstituted by identical or different substituents from the group consisting of fluorine, chlorine and bromine, or phenyl which is unsubstituted or monosubstituted to trisubstituted by identical or different substituents from the group consisting of fluorine, chlorine, nitro, methyl, methoxy, trifluoromethyl, methylamino, dimethylamino and phenylmethoxy; further alkyl substituents are cyclopropyl, cyclohexyl or cyclohexenyl, each of which is unsubstituted or monosubstituted or disubstituted by methyl or chlorine, or a heterocyclic ring of the formula

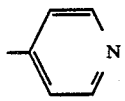

which is unsubstituted or monosubstituted to trisubstituted by methyl, $R^1$ furthermore represents allyl or propargyl, each of which is substituted by phenyl, or represents cyclohexyl, cyclopropyl or cyclohexenyl, each of which is unsubstituted or monosubstituted or disubstituted by methyl or chlorine, $R^2$ represents hydrogen, or represents methyl or ethyl, each of which is unsubstituted or monosubstituted to trisubstituted by identical or different substituents selected from the group consisting of fluorine, chlorine, cyano, —COOH, —COOR$^3$, —CONR$^4$R$^5$, —OR$^6$, —SR$^6$, alkylcarbonyl which has 1 to 5 carbon atoms, phenyl, cyclopropyl, 1,3-dioxolan-2-yl, 1,2,4-triazol-1-yl and phenylcarbonyl which is unsubstituted or monosubstituted or disubstituted by identical or different substituents from the group consisting of fluorine, chlorine and bromine; $R^2$ furthermore represents allyl or propargyl, or represents cyclohexyl or phenyl which is unsubstituted or monosubstituted or disubstituted by identical or different substituents from the group consisting of chlorine, methyl and methoxy, or represents one of the radicals —CX—YR$^3$, —CXNR$^4$R$^5$, —COR$^6$, —SO$_2$—NR$^4$R$^5$ or —SO$_2$R$^7$ where X and Y are identical or different and represent oxygen or sulphur, $R^3$ represents methyl, ethyl, n- or i-propyl or n-, i-, s- or t-butyl, $R^4$ represents hydrogen, methyl, ethyl, n- or i-propyl, n-, i-, s- or t-butyl or phenyl, $R^5$ represents hydrogen, methyl, ethyl, n- or i-propyl, n-, i-, s- or t-butyl or phenyl, $R^6$ represents hydrogen or methyl, ethyl, n- or i-propyl or n-, i-, s- or t-butyl, each of which is unsubstituted or monosubstituted to trisubstituted by fluorine, chlorine, methoxy or phenyl, $R^6$ furthermore represents phenyl, methoxycarbonyl, ethoxycarbonyl or phenylcarbonyl and $R^7$ represents methyl, ethyl, n- or i-propyl or n-, i-, s- or t-butyl, or represents phenyl which is unsubstituted or monosubstituted or disubstituted by methyl.

5. A substituted 3-amino-2-pyrazolin-5-one derivative according to claim 1, in which $R^1$ represents straight-chain or branched alkyl which has 1 to 6 carbon atoms and which is unsubstituted, or represents methyl, ethyl or n- or i-propyl, each of which is monosubstituted or disubstituted by identical or different substituents selected from the group consisting of fluorine, cyano, —COOH, —COOR$^3$, —CONR$^4$R$^5$, —OR$^6$, —SR$^6$, alkylcarbonyl which has 1 to 5 carbon atoms in the alkyl moiety, phenylcarbonyl which is unsubstituted or monosubstituted or disubstituted by bromine substituents, phenyl which is unsubstituted or monosubstituted to trisubstituted by identical or different substituents from the group consisting of chlorine, methyl, methoxy, nitro, dimethylamino, benzyloxy and trifluoromethyl, and cyclopropyl, cyclohexyl or cyclohexenyl, or cyclopropyl which is monosubstituted or disubstituted by identical or different substituents from the group consisting of chlorine and methyl, or a heterocyclic ring of the formula

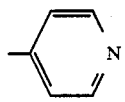

which is unsubstituted or monosubstituted to trisubstituted by methyl, $R^1$ furthermore represents allyl, phenylallyl, propargyl, cyclohexyl or cyclohexenyl, $R^2$ represents hydrogen, or alkyl which has 1 to 4 carbon atoms and which is straight-chain or branched, or alkylcarbonyl which has 1 to 3 carbon atoms in the straight-chain or branched alkyl moiety, or alkylaminocarbonyl which has 1 to 2 carbon atoms in the alkyl moiety, or represents straight-chain or branched alkyl which has 1 to 3 carbon atoms and which is monosubstituted by alkoxy or alkoxycarbonyl having 1 to 3 carbon atoms in the alkoxy moiety, cyano, hydroxyl, aminocarbonyl, phenyl, —COOH, phenylcarbonyl, cyclopropyl, triazolyl or dioxolanyl, halogenoalkyl which has 1 to 3 carbon atoms and 1 to 5 identical or different halogen atoms, or phenylsulphonyl, phenyl or phenyl which is monosubstituted to trisubstituted by identical or different substituents from the group consisting of chlorine and methyl, or alkylthiocarbonyl which has 1 to 3 carbon atoms in the straight-chain or branched alkylthio moiety, or alkenyl or alkinyl, each of which has 3 to 4 carbon atoms, $R^3$ represents methyl, ethyl, n- or i-propyl or n-, i-, s- or t-butyl, $R^4$ represents hydrogen, methyl, ethyl, n- or i-propyl, n-, i-, s- or t-butyl or phenyl, $R^5$ represents hydrogen, methyl, ethyl, n- or i-propyl, n-, i-, s- or t-butyl of phenyl, and $R^6$ represents hydrogen or methyl, ethyl, n- or i-propyl or n-, i-, s- or t-butyl, each of which is substituted or monosubstituted to trisubstituted by fluorine, chlorine, methoxy or phenyl, or $R^6$ furthermore represents phenyl, methoxycarbonyl, ethoxycarbonyl or phenylcarbonyl.

6. A compound according to claim 1, wherein such compound is 3-amino-4-benzyloximino-2-pyrazolin-5-one of the formula

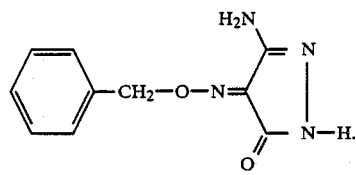

7. A compound according to claim 1, wherein such compound is 3-amino-4-(2-chlorobenzyloximino)-2-pyrazolin-5-one of the formula

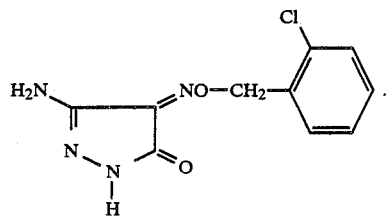

8. A compound according to claim 1, wherein such compound is 3-amino-4-(3,4-dichlorobenzyloximino)-2-pyrazolin-5-one of the formula

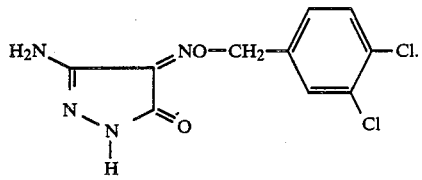

9. A compound according to claim 1, wherein such compound is 3-amino-4-phenethyloximino-2-pyrazolin-5-one of the formula

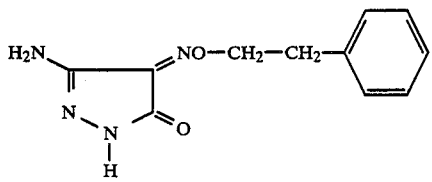

10. A compound according to claim 1, wherein such compound is 3-amino-4-(4-methylbenzyloximino)-2-pyrazolin-5-one of the formula

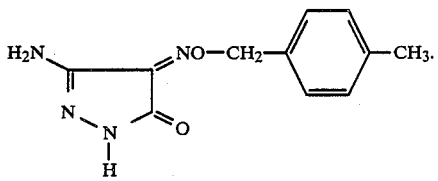

11. A fungicidal composition comprising a fungicidally effective amount of a substituted 3-amino-2-pyrazolin-5-one derivative according to claim 1 and a diluent.

12. A method of combating fungi which comprises applying to such fungi or to a fungus habitat a fungicidally effective amount of a substituted 3-amino-2-pyrazolin-5-one derivative according to claim 1.

13. The method according to claim 12, wherein such compound is
3-amino-4-benzyloximino-2-pyrazolin-5-one,
3-amino-4-(2-chlorobenzyloximino)-2-pyrazolin-5-one,
3-amino-4-(3,4-dichlorobenzyloximino)-2-pyrazolin-5-one,
3-amino-4-phenethyloximino-2-pyrazolin-5-one. or
3-amino-4-(4-methylbenzyloximino)-2-pyrazolin-5-one.

* * * * *